(12) United States Patent
Saidi

(10) Patent No.: US 11,564,042 B2
(45) Date of Patent: Jan. 24, 2023

(54) APPARATUS FOR MANIPULATION OF EAR DEVICES

(71) Applicants: EARPLACE INC., Dunn Loring, VA (US); Iyad Saidi, Dunn Loring, VA (US)

(72) Inventor: Iyad Saidi, Dunn Loring, VA (US)

(73) Assignee: EARPLACE INC., Dunn Loring, VA (US)

( * ) Notice: Subject to any disclaimer, the term of this patent is extended or adjusted under 35 U.S.C. 154(b) by 798 days.

(21) Appl. No.: 16/465,883

(22) PCT Filed: Dec. 1, 2017

(86) PCT No.: PCT/US2017/064180
§ 371 (c)(1),
(2) Date: May 31, 2019

(87) PCT Pub. No.: WO2018/102664
PCT Pub. Date: Jun. 7, 2018

(65) Prior Publication Data
US 2020/0000406 A1 Jan. 2, 2020

Related U.S. Application Data

(60) Provisional application No. 62/577,527, filed on Oct. 26, 2017, provisional application No. 62/428,697, filed on Dec. 1, 2016.

(51) Int. Cl.
*H04R 25/00* (2006.01)
*A61B 5/01* (2006.01)
(Continued)

(52) U.S. Cl.
CPC ............... *H04R 25/00* (2013.01); *A61B 5/01* (2013.01); *A61B 5/02438* (2013.01); *A61B 5/14532* (2013.01); *A61B 5/14542* (2013.01); *A61B 5/14546* (2013.01); *A61B 5/369* (2021.01); *A61B 5/6816* (2013.01); *A61B 5/6817* (2013.01); *A61B 5/7275* (2013.01); *A61N 2/006* (2013.01); *A61N 2/02* (2013.01);
(Continued)

(58) Field of Classification Search
None
See application file for complete search history.

(56) References Cited

U.S. PATENT DOCUMENTS 2,706,927 A   4/1955  Howard et al.
3,412,729 A   11/1968 Smith, Jr. et al.
(Continued)

OTHER PUBLICATIONS

Vadalà et al Mechanisms and therapeutic applications of electromagnetic therapy in Parkinson's disease Behav Brain Funct (2015) 11:26 (Year: 2015).*

(Continued)

*Primary Examiner* — Jay B Shah
(74) *Attorney, Agent, or Firm* — Wilson Sonsini Goodrich & Rosati

(57) ABSTRACT

Disclosed herein are apparatuses for manipulation of an ear device within the ear canal of a subject. Also disclosed herein are methods of using said apparatuses for the insertion, removal, or other manipulations of the ear device. Also disclosed herein are methods of making the apparatuses, and kits containing the apparatus with instructions for use.

18 Claims, 16 Drawing Sheets

(51) Int. Cl.
*A61B 5/024* (2006.01)
*A61B 5/145* (2006.01)
*A61B 5/00* (2006.01)
*A61N 2/00* (2006.01)
*A61N 2/02* (2006.01)
*G10K 11/178* (2006.01)
*A61B 5/369* (2021.01)

(52) U.S. Cl.
CPC ......... *G10K 11/178* (2013.01); *H04R 25/554* (2013.01); *H04R 25/75* (2013.01); *A61B 2503/06* (2013.01); *A61B 2503/12* (2013.01); *A61B 2503/40* (2013.01); *A61B 2560/0475* (2013.01); *A61B 2560/063* (2013.01); *G10K 2210/1081* (2013.01); *H04R 25/603* (2019.05); *H04R 25/652* (2013.01); *H04R 25/658* (2013.01); *H04R 2225/023* (2013.01); *H04R 2225/61* (2013.01); *H04R 2460/17* (2013.01)

(56) References Cited

U.S. PATENT DOCUMENTS

| | | | |
|---|---|---|---|
| 4,756,312 | A | 7/1988 | Epley |
| 5,003,608 | A | 3/1991 | Carlson |
| 6,055,319 | A | 4/2000 | Shennib et al. |
| 7,676,372 | B1 | 3/2010 | Oba |
| 8,155,361 | B2 | 4/2012 | Schindler |
| 8,411,889 | B2 | 4/2013 | Naumann et al. |
| 8,457,337 | B2 | 6/2013 | Michel et al. |
| 8,527,280 | B2 | 9/2013 | Boesen |
| 2003/0065504 | A1 | 4/2003 | Kraemer et al. |
| 2005/0249370 | A1 | 11/2005 | Shennib et al. |
| 2006/0126876 | A1 | 6/2006 | Shennib |
| 2009/0116676 | A1* | 5/2009 | Welsh .............. H04R 1/24 381/380 |
| 2011/0004089 | A1 | 1/2011 | Chou |
| 2011/0180947 | A1* | 7/2011 | Kwon ............... H04R 25/658 264/40.1 |
| 2011/0206225 | A1 | 8/2011 | Moeller et al. |
| 2012/0308060 | A1 | 12/2012 | Pontoppidan |
| 2013/0223666 | A1 | 8/2013 | Michel et al. |
| 2014/0073835 | A1 | 3/2014 | Shapiro et al. |
| 2014/0270300 | A1 | 9/2014 | Michel et al. |
| 2015/0195639 | A1 | 7/2015 | Azmi et al. |
| 2016/0171966 | A1* | 6/2016 | Molinari .......... G10K 11/17827 381/71.11 |
| 2016/0192050 | A1 | 6/2016 | Masaki et al. |

OTHER PUBLICATIONS

International Preliminary Report on Patentability dated Jun. 4, 2019 for International Application Serial No. PCT/US2017/064180, (21 pages).

International Search Report dated Mar. 19, 2018 for International Application Serial No. PCT/US2017/064180, (5 pages).

Written Opinion of the International Searching Authority dated Mar. 19, 2018 for International Application Serial No. PCT/US2017/064180, (20 pages).

Supplementary European Search Report dated May 19, 2020 for Application No. EP 17 87 5211, (8 pages).

* cited by examiner

APPARATUS FOR MANIPULATION OF EAR DEVICES

CROSS-REFERENCE

This application claims the benefit of U.S. Provisional Application No. 62/428,697, filed on Dec. 1, 2016, and U.S. Provisional Application No. 62/577,527, filed on Oct. 26, 2017, which applications are incorporated herein by reference in their entirety.

SUMMARY

Disclosed herein are apparatuses comprising: (a) an elongated section; (b) a stop section associated with the elongated section; where the stop section can contact a portion of an ear of the subject when the elongated section is inserted into the ear of the subject, thereby preventing further insertion of the elongated section into the ear of the subject; (c) an electromagnet associated with a first end of the elongated section; where the electromagnet can be magnetically attracted to a magnetic element associated with the ear device; and (d) a power source and a switch electronically connected to the electromagnet; where the switch can turn the electromagnet on and off.

Disclosed herein are apparatuses comprising: (a) an elongated section; (b) a stop section associated with the elongated section; where the stop section contacts a portion of an ear of a subject when the elongated section is inserted into an ear of the subject, thereby preventing further insertion of the elongated section into the ear of the subject; and (c) a magnet associated with a first end of the elongated section; where the magnet is magnetically attracted to a magnetic element associated with an ear device. In some embodiments, the apparatus is configured to hold the ear device via at least a magnetic attraction between the magnet and the magnetic element of the ear device during the insertion of the apparatus into the ear, thereby inserting the ear device into the ear. In some embodiments, the ear device is sized to the ear of the subject, such that when the ear device is inserted in the ear at a predetermined position and the apparatus is removed from the ear of the subject, a friction between the ear and the ear device overcomes the magnetic attraction to detach the ear device from the apparatus, thereby retaining the ear device at the predetermined position. In some embodiments, the magnet can be a permanent magnet.

In some embodiments, the elongated section can be an arm. In some embodiments, the stop section can be a flange. In some embodiments, the flange can comprise a handle. In some embodiments, the stop section can be associated with a second end of the elongated section.

In some embodiments, the apparatus can be an apparatus for inserting an ear device. In some embodiments, the apparatus can be an apparatus for removing an ear device. In some embodiments, the apparatus can be an apparatus for manipulating an ear device.

In some embodiments, the ear device can comprise a storage medium. In some cases, the storage medium can be a flash memory.

In some embodiments, the magnetic element of the ear device can be a ferromagnetic element. In some embodiments, the magnetic element of the ear device can be a ferrimagnetic element. In some embodiments, the magnetic element of the ear device can be an antiferromagnetic element.

In some embodiments, the ear device can be a communication device. In some cases, the communication device can be a recording device. In some cases, the communication device can be a transmission device. In some cases, the transmission device can be a device for transmitting a location. In some cases, the transmission device can transmit signals electronically. In some cases, the communication device can be a receiving device. In some cases, the receiving device can be a device for receiving a location. In some cases, the receiving device can receive signals electronically. In some cases, the communication device can be a translation device. In some cases, the communication device can be a key fob. In some cases, the key fob can be used for authentication. In some cases, the communication device can be an authentication device.

In some embodiments, the ear device can be a magnet.

In some embodiments, the ear device can be an earplug. In some cases, the earplug can comprise a foam material. In some cases, the earplug can at least partially regulate pressure transmitted into the ear of the subject. In some cases, the earplug can at least partially regulate sound waves transmitted into the ear of the subject.

In some embodiments, the ear device can further comprise a noise canceling element, where the noise canceling element transmits destructive interference when engaged. In some cases, the destructive interference can at least partially ameliorate tinnitus.

In some embodiments, the ear device can further comprise a magnetic field generator. In some cases, the magnetic field generator can at least partially ameliorate a disorder when engaged. In some cases, the disorder can be selected from the group consisting of a migraine; a loss of taste; a loss of smell; Parkinson disease; a depression disorder; major depression disorder; and any combination thereof.

In some embodiments, the ear device can be a diagnostic device. In some cases, the diagnostic device can detect electrical signals in a brain of the subject. In some cases, the diagnostic device can detect a signal that correlates to a dissolved oxygen level in a blood vessel of the subject. In some cases, the diagnostic device can detect a signal that correlates to a pulse of the subject. In some cases, the diagnostic device can detect a signal that correlates to a glucose level in a blood vessel of the subject. In some cases, the diagnostic device can detect a signal that correlates to a body temperature of the subject. In some cases, the diagnostic device can detect a signal that correlates to a salinity level in a blood vessel of the subject. In some cases, the detection can further comprise a determination of a likelihood of a cardiovascular disease. In some cases, the cardiovascular disease can comprise a stroke. In some cases, the cardiovascular disease can comprise a heart attack.

In some embodiments, the subject can be a mammal. In some cases, the mammal can be selected from the group consisting of a primate, a horse, a cat, a dog, a cow, and a rodent. In some cases, the subject can be a human. In some cases, the human can be an adult. In some cases, the human can be a child. In some cases, the human can be from about age 0 to 18 years old. In some cases, the human can be from about age 18 to 130 years old.

In some embodiments, the ear device can comprise jewelry. In some cases, the ear device can be an earring. In some cases, the jewelry can be non-piercing.

In some embodiments, the ear device can comprise an outer layer of cotton.

In some embodiments, the elongated section can be flexible. In some embodiments, the elongated section can be semi-flexible. In some embodiments, the elongated section can be rigid. In some cases, the elongated section can be composed at least in part of a material selected from the group consisting of a plastic, a silicon, a wood, a metal, a rubber, a thermoplastic polyurethane, a graphene, an aluminum mesh, a stone, a titanium compound, a paper, a marble, a cloth, a carbon fiber, a wax, gold, silver, platinum, palladium, tungsten, stainless steel, a jewel, and any combination thereof. In some cases, the elongated section can be composed at least in part of recyclable material. In some cases, the elongated section can be custom molded to the subject's ear.

In some embodiments, the elongated section can be at least partially collapsible. In some cases, the elongated section when at least partially collapsed can have a length of at most about 3 cm, at most about 2.5 cm, at most about 2 cm, at most about 1.5 cm, at most about 1 cm, at most about 0.5 cm, at most about 0.4 cm, at most about 0.3 cm, at most about 0.2 cm, at most about 0.1 cm, or at most about 0.05 cm.

In some embodiments, the apparatus can be at least partially reusable. In some embodiments, the apparatus can be at least partially a single use apparatus. In some embodiments, the apparatus can be at least partially biodegradable.

In some embodiments, the apparatus can further comprise a light. In some cases, the apparatus can further comprise a camera.

In some embodiments, the elongated section does not comprise a pin, a metal rod, a spring, or a combination thereof disposed in the elongated section.

In some embodiments, the electromagnet can be attached to the first end of the elongated section in a fixed manner. In some embodiments, the electromagnet can be at least partially rotatable along the first end of the elongated section. In some embodiments, the apparatus can further comprise at least one additional magnet. In some cases, the apparatus can comprise an array of magnets. In some cases, the array of magnets can be configured to actuate sequentially.

In some embodiments, the elongated section and the stop section can constitute a part of a conical article.

In some embodiments, the stop section can have a diameter greater than a diameter of a subject's ear canal.

In some embodiments, the conical article can be flexible.

In some embodiments, the conical article can be semi-flexible.

In some embodiments, the conical article can be rigid.

In some embodiments, the apparatus can comprise an orientation restriction section that is configured to maintain an orientation of the ear device consistent with an orientation of the apparatus during insertion of the ear device into the ear.

In some embodiments, the orientation restriction section can restrict the orientation of the ear device at least in part by mechanical force, electrostatic force, magnetic force, or any combination thereof.

In some embodiments, the orientation restriction section can comprise a hollow structure adapted to engage at least part of the ear device.

In some embodiments, the orientation restriction section can be an extension of the elongated section of the apparatus.

Also disclosed herein are methods of inserting an ear device comprising a magnetic element into an ear of a subject, comprising inserting an apparatus disclosed herein into the ear of the subject, where the apparatus can be in contact with the magnetic element of the ear device through a magnetic attraction.

In some embodiments, the method can further comprise activating the switch on the apparatus and thereby turning off the electromagnet; thereby removing the magnetic attraction between the magnetic element of the ear device and the electromagnet.

In some embodiments, the method can further comprise removing the apparatus.

Also disclosed herein are methods of removing an ear device, comprising a magnetic element from an ear of a subject, comprising: (a) inserting an apparatus disclosed herein into the ear of the subject; (b) activating the electromagnet; thereby providing a magnetic attraction between the magnetic element of the ear device and the electromagnet; and (c) removing the apparatus.

In some embodiments, the method can further comprise activating a switch on the apparatus prior to (b).

In some embodiments, the magnetic element can be associated with the ear device through a linker, and the removing can comprise: (a) removing the apparatus until the magnetic element and at least a portion of the linker are outside of the ear; and (b) removing the ear device. In some embodiments, the removing the device can comprise pulling the magnetic element, the linker, or both until the ear device is removed out of the ear.

Also disclosed herein are methods of manipulating an ear device that comprises a magnetic element, comprising: (a) providing an insertion apparatus, the insertion apparatus comprising (1) an elongated section; (2) a stop section associated with the elongated section; wherein the stop section contacts a portion of the ear when the elongated section is inserted into an ear of the subject, thereby preventing further insertion of the elongated section into the ear of the subject; and (3) a magnet associated with a first end of the elongated section; wherein the magnet is magnetically attracted to the magnetic element of the ear device; (b) inserting the insertion apparatus into the ear of the subject, wherein the insertion apparatus is configured to hold the ear device during the insertion via at least a magnetic attraction between the magnet and the magnetic element of the ear device, thereby inserting the ear device into the ear, and (c) removing the insertion apparatus from the ear of the subject after the ear device is inserted in the ear at a predetermined position, wherein the ear device is sized to the ear of the subject, such that when the ear device is inserted at the predetermined position and the insertion apparatus is removed from the ear, a friction between the ear and the ear device overcomes the magnetic attraction to detach the ear device from the apparatus, thereby retaining the ear device at the predetermined position.

In some embodiments, the method of manipulating the ear device can further comprise: (d) providing a removal apparatus, the removal apparatus comprising an elongated section and a magnet associated with a first end of the elongated section; (e) inserting the removal apparatus into the ear of the subject in such a manner to produce a magnetic attraction between the magnet of the removal apparatus and the ear device; and (f) removing the removal apparatus from the ear of the subject, wherein the removal apparatus is configured to hold the ear device during the removal via at least a magnetic attraction between the removal apparatus and the magnetic element of the device, and wherein the magnetic attraction is configured to overcome the friction, thereby pulling the ear device out of the ear when the apparatus is being removed from the ear. In some embodiments, the magnet can be a permanent magnet.

Also disclosed herein are methods of manipulating an ear device in an ear of a subject, where the ear device can comprise a magnetic element, comprising: (a) inserting an apparatus disclosed herein into the ear of the subject; (b) activating the electromagnet; thereby providing a magnetic attraction between the magnetic element of the ear device and the electromagnet; and (c) manipulating the apparatus; thereby manipulating the ear device in the ear of the subject.

In some embodiments, the manipulating of the ear device can be a rotation of the ear device. In some cases, the manipulating of the ear device can be a distal translation of ear device. In some cases, the manipulating of the ear device can be a proximal translation of the ear device.

Also disclosed herein are methods of concealing an ear device comprising a magnetic element deep into an ear of a subject comprising: (a) inserting an apparatus disclosed herein into the ear of the subject, where the apparatus can be in contact with the magnetic element of the ear device through a magnetic attraction; (b) deactivating the electromagnet; thereby removing the magnetic attraction between the magnetic element of the ear device and the electromagnet; and (c) removing the apparatus; where the ear device, when inserted, is not visible to unaided human eyes from the outside of the ear; thereby concealing the ear device within the ear of the subject.

In some embodiments, the method can further comprise activating a switch on the apparatus prior to (b).

Also disclosed herein are methods of ameliorating loss of a magnetic wireless earphone comprising: (a) inserting an apparatus disclosed herein into the ear of the subject, where the apparatus can be in contact with the magnetic element of the ear device through a magnetic attraction; (b) deactivating the electromagnet; thereby removing the magnetic attraction between the magnetic element of the ear device and the electromagnet; (c) removing the apparatus; and (d) inserting the magnetic wireless earphone into the ear of the subject; where the ear device can be a magnet, and where the magnetic wireless earphone can be magnetically attracted to the ear device.

In some embodiments, the method can further comprise activating a switch on the apparatus prior to (b).

Also disclosed herein are kits, comprising: (a) an apparatus disclosed herein; and (b) instructions for use.

In some embodiments, the kit can further comprise an ear device. In some instances, the ear device can comprise a storage medium. In some cases, the storage medium can be a flash memory. In some instances, the ear device can be a communication device. In some cases, the communication device can be a recording device. In some cases, the communication device can be a transmission device. In some cases, the communication device can be a translation device. In some instances, the ear device can be an earplug. In some cases, the earplug can comprise a foam material. In some cases, the earplug can at least partially regulate pressure transmitted into the ear of the subject. In some cases, the earplug can at least partially regulate sound waves transmitted into the ear of the subject. In some instances, the ear device can further comprise a noise canceling element, where the noise canceling element can transmit destructive interference when engaged. In some cases, the destructive interference can at least partially ameliorate tinnitus. In some instances, the ear device can further comprise a magnetic field generator. In some cases, the magnetic field generator can at least partially ameliorate a disorder when engaged. In some cases, the disorder can be selected from the group consisting of a migraine; a loss of taste; a loss of smell; Parkinson disease; a depression disorder; major depression disorder; and any combination thereof. In some instances, the ear device can be a diagnostic device. In some cases, the diagnostic device can detect electrical signals in a brain of the subject. In some cases, the diagnostic device can detect a signal that correlates to a dissolved oxygen level in a blood vessel of the subject. In some cases, the diagnostic device can detect a signal that correlates to a pulse of the subject. In some cases, the detection can further comprise a determination of a likelihood of a cardiovascular disease. In some cases, the cardiovascular disease can comprise a stroke. In some cases, the cardiovascular disease can comprise a heart attack. In some instances, the ear device can be in wireless communication with another device. In some cases, the wireless communication can be selected from the group consisting of Bluetooth, Wi-Fi, a mobile network, and any combination thereof. In some instances, the ear device can comprise jewelry. In some cases, the ear device can be an earring. In some cases, the jewelry can be non-piercing. In some cases, the ear device can comprise an outer layer of cotton.

Also disclosed herein are methods of making a kit comprising: (a) packaging an apparatus disclosed herein; and (b) combining the apparatus of (a) with instructions for use.

In some embodiments, the method can further comprise combining the apparatus of (a) with an ear device.

Also disclosed herein are methods of manufacturing an apparatus, comprising: (a) attaching an electromagnet to a first end of an elongated section of the apparatus; and (b) electrically connecting a power source and a switch to the electromagnet, where the switch turns the electromagnet on and off.

In some embodiments, the method can further comprise attaching a stop section to a second end of the elongated section of the apparatus; where the stop section contacts a portion of an ear of a subject when the elongated section is inserted into the ear of the subject, thereby preventing further insertion of the elongated section into the ear of the subject.

Also disclosed herein are ear devices, comprising a magnetic switch, the magnetic switch being maneuverable by a magnetic force to switch the ear device between different work modes.

In some embodiments, at the different work modes, the ear device can regulate pressure or acoustic waves transmitted therethrough at different efficiencies.

Also disclosed herein are kits, comprising an apparatus disclosed herein, and an ear device that comprises a magnetic switch, the magnetic switch being maneuverable by a magnetic force to switch the ear device between different work modes. In some embodiments, at the different work modes, the ear device can regulate pressure or acoustic waves transmitted therethrough at different efficiencies.

Also disclosed herein are methods, comprising: (a) providing an ear device disclosed herein; (b) inserting an apparatus disclosed herein that comprises the electromagnet; (c) activating the electromagnet to provide a magnetic attraction between the electromagnet and the magnetic switch of the ear device; and (c) maneuvering the magnetic switch to change the work mode of the ear device.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of embodiments are set forth with particularity in the appended claims. A better understanding of features and advantages will be obtained by reference to the following detailed description that sets forth illustrative embodiments, in which the principles of said embodiments are utilized, and the accompanying drawings of which:

FIG. 11A shows an insertion device in magnetic attraction with the ear device. FIG. 11B shows a removal device that can be used to remove the ear device from the ear canal. As shown in FIG. 11C, the magnetic element can be removed from the ear canal without removing the entire ear device. The ear device can be removed from the ear canal by pulling on the magnetic element attached to the ear device by the spring.

DETAILED DESCRIPTION

I. Overview

Figure 1:
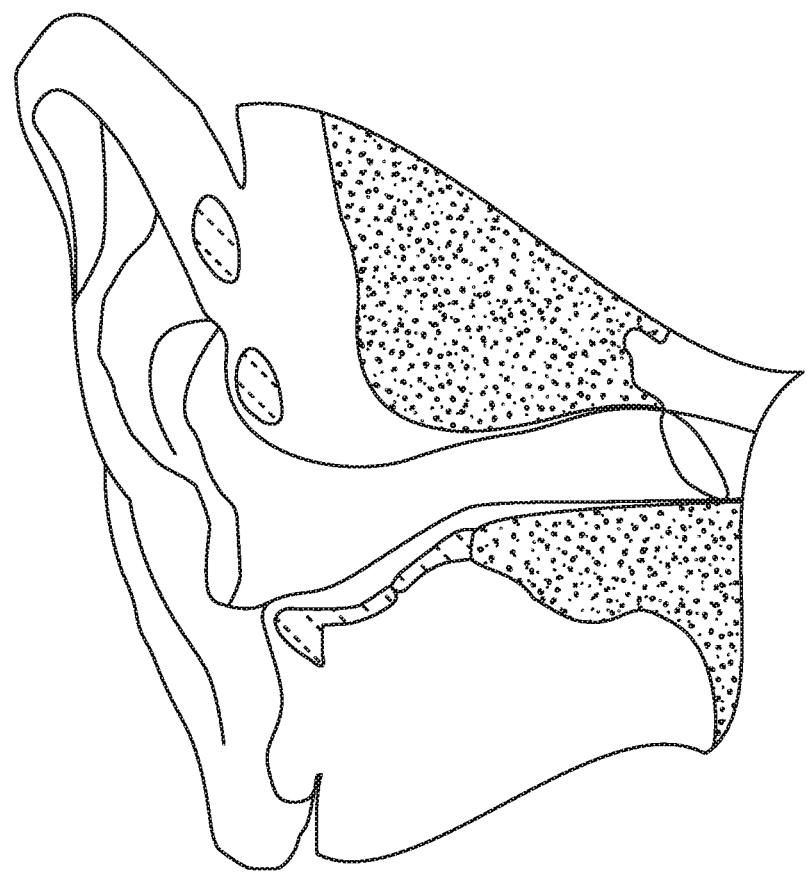
FIG. 1 depicts a diagram of the ear canal.

FIG. 1 depicts an illustration of an ear canal. Disclosed herein are apparatuses for manipulation of ear devices in an ear canal of a subject. In some instances, the apparatuses can comprise: (a) an elongated section; (b) a stop section associated with the elongated section; where the stop section contacts a portion of an ear of the subject when the elongated section is inserted into the ear of the subject, thereby preventing further insertion of the elongated section into the ear of the subject; (c) an electromagnet associated with a first end of the elongated section; where the electromagnet is magnetically attracted to a magnetic element associated with the ear device; and (d) a power source and a switch electronically connected to the electromagnet; where the switch turns the electromagnet on and off.

In some embodiments, the apparatus can comprise: (a) a conical article having a narrow end and a wide end; (b) an electromagnet associated with the narrow end of the conical article; where the electromagnet is magnetically attracted to a magnetic element associated with an ear device; and (c) a power source and a switch electronically connected to the electromagnet; where the switch turns the electromagnet on and off.

Also disclosed herein are methods of using the apparatus to insert an ear device into an ear of a subject, comprising inserting an apparatus described herein in association with an ear device into the ear of the subject.

Also disclosed herein are methods of using the apparatus to remove an ear device from an ear of a subject, comprising: (a) inserting an apparatus described herein into the ear of the subject; (b) activating the electromagnet; thereby providing a magnetic attraction between the magnetic element of the ear device and the electromagnet; and (c) removing the apparatus.

Also disclosed herein are methods of manipulating an ear device in an ear of a subject, where the ear device can comprise a magnetic element, comprising: (a) inserting an apparatus described herein into the ear of the subject; (b) activating the electromagnet; thereby providing a magnetic attraction between the magnetic element of the ear device and the electromagnet; and (c) manipulating the apparatus; thereby manipulating the ear device in the ear of the subject.

Also disclosed herein are methods of concealing an ear device comprising a magnetic element deep into an ear of a subject comprising: (a) inserting an apparatus described herein into the ear of the subject, where the apparatus is in contact with the magnetic element of the ear device through a magnetic attraction; (b) deactivating the electromagnet; thereby removing the magnetic attraction between the magnetic element of the ear device and the electromagnet; and (c) removing the apparatus; where the ear device, when inserted, is not visible from the outside of the ear; thereby concealing the ear device within the ear of the subject.

Also disclosed herein are methods of ameliorating loss of a magnetic wireless earphone comprising: (a) inserting an apparatus disclosed herein into the ear of the subject, where the ear device is magnet and can comprise a magnetic element, and where the apparatus is in contact with the magnetic element of the ear device through a magnetic attraction; (b) deactivating the electromagnet; thereby removing the magnetic attraction between the magnetic element of the ear device and the electromagnet; (c) removing the apparatus; and (d) inserting the magnetic wireless earphone into the ear of the subject; where the magnetic wireless earphone is magnetically attracted to the ear device.

Also disclosed herein are kits, comprising an apparatus disclosed herein and instructions for use. In some embodiments, the kit can further comprise an ear device.

Also disclosed herein are methods of making a kit comprising (a) packaging an apparatus described herein; and combining the apparatus of (a) with instructions for use.

Also disclosed herein are methods of manufacturing an apparatus, comprising: (a) attaching an electromagnet to a first end of an elongated section of the apparatus; and (b) electrically connecting a power source and a switch to the electromagnet, where the switch turns the electromagnet on and off.

II. Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e., the limitations of the measurement system. For example, "about" can mean about plus or minus 10%, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed. Also, where ranges and/or subranges of values are provided, the ranges and/or subranges can include the endpoints of the ranges and/or subranges.

The term "subject", "patient" or "individual" as used herein in reference to an individual, and can encompass a mammal and a non-mammal. A mammal can be any member of the Mammalian class, including but not limited to a human, a non-human primates such as a chimpanzee, an ape or other monkey species; a farm animal such as cattle, a cow, a horse, a sheep, a goat, a swine; a domestic animal such as a rabbit, a dog, and a cat; a laboratory animal including a rodent, such as a rat, a mouse and a guinea pig, and the like. A non-mammal can include a bird, a fish and the like. In some embodiments, a subject can be a mammal. In some embodiments, a subject can be a human. In some instances, the human can be an adult. In some instances, the human can be a child. In some instances, the human can be from about age 0 to 18 years old. In some instances, the human can be from about age 18 to 130 years old.

In some cases, the terms "subject" and "user" can be used interchangeably to describe the individual in which an apparatus described herein is used to manipulate an ear device in the ear canal of the individual. In some cases, the "subject" and "user" can be different individuals. For example, a subject can be the individual whom an apparatus described herein is used to manipulate an ear device in the ear canal of the individual while a user can be an individual that inserts or monitors the ear device after insertion in the subject's ear.

The terms "treat," "treating", "treatment," "ameliorate" or "ameliorating" and other grammatical equivalents as used herein, can include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms can further include achieving a therapeutic benefit and/or a prophylactic benefit. Therapeutic benefit can mean eradication or amelioration of the underlying disease being treated. Also, a therapeutic benefit can be achieved with the eradication or amelioration of one or more of the physiological symptoms associated with the underlying disease such that an improvement can be observed in the patient, notwithstanding that, in some embodiments, the patient can still be afflicted with the underlying disease.

The terms "communication," "communicated," "in communication with," "transmission," and "receiving" can refer to electronic exchange or communication between a pair of devices. In some instances, the exchange can occur though a wired connection between the pair of devices such as through the use of a USB cord or fiber optic connection. In some instances, the exchange can occur through a wireless connection between the pair of devices. In some cases, a wireless signal can be sent through a mobile data network such as a 4G LTE or 3G data signal. In some cases, a wireless signal can be sent through a Bluetooth connection. In some cases, a wireless signal can be sent through a Wi-Fi connection. In some cases, a wireless signal can be sent through an infra-red data association link.

The term "electromagnet" can refer to a type of magnet in which the magnetic field is produced by an electric current. In some cases, the electromagnet can be made from a coil of wire that acts as a magnet when an electric current passes through it but stops being a magnet when the current stops. The terms "static magnet" and "permanent magnet", as used interchangeably herein, can refer to an object made from a material that is magnetized and creates magnetic field with no need of electric current passing through it.

The term "mechanical force" can refer to a contact force applied to an object that involves tension, pressure, friction, shear, or any combinations thereof. The term "electrostatic force" can refer to an attraction or repulsion of an object because of its electric charge, for instance, two objects with like electric charges, both positive or both negative, repel each other, while two objects with opposite electric charges, attract each other. The term "magnetic force", in some cases, can refer to an attraction or repulsion that arises between electrically charged particles because of their motion.

III. Apparatus

Figure 2:
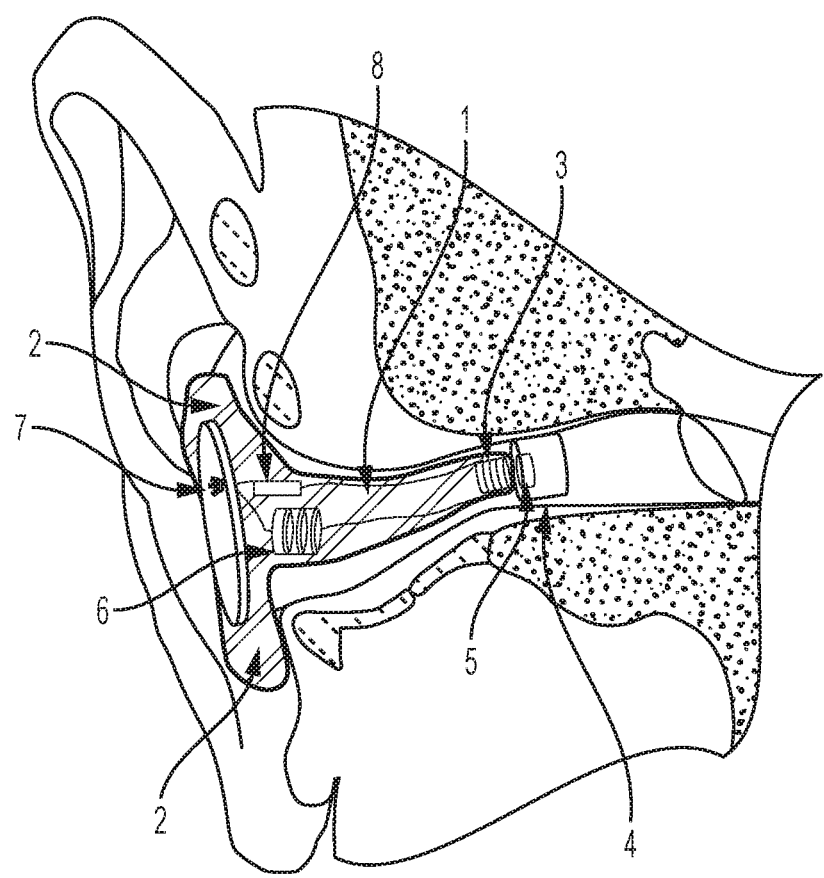
FIG. 2 depicts an ear device containing a magnetic element in association with an apparatus described herein.

Disclosed herein are apparatuses for manipulation of an ear device in an ear of a subject. FIG. 2 depicts an embodiment of an apparatus described herein, which can comprise an elongated section 1; a stop section 2 associated with the elongated section 1 along a second or proximal end; where the stop section 2 contacts a portion of an ear of the subject when the elongated section 1 is inserted into the ear of the subject, thereby preventing further insertion of the elongated section 1 into the ear of the subject; an electromagnet 3 associated with a first or distal end of the elongated section 1; where the electromagnet 3 is magnetically attracted to a magnetic element 5 associated with the ear device 4; and a power source 6 and a switch 7 electronically connected to the electromagnet 3 through a control circuit 8; where the switch 7 turns the electromagnet 3 on and off.

Figure 3:
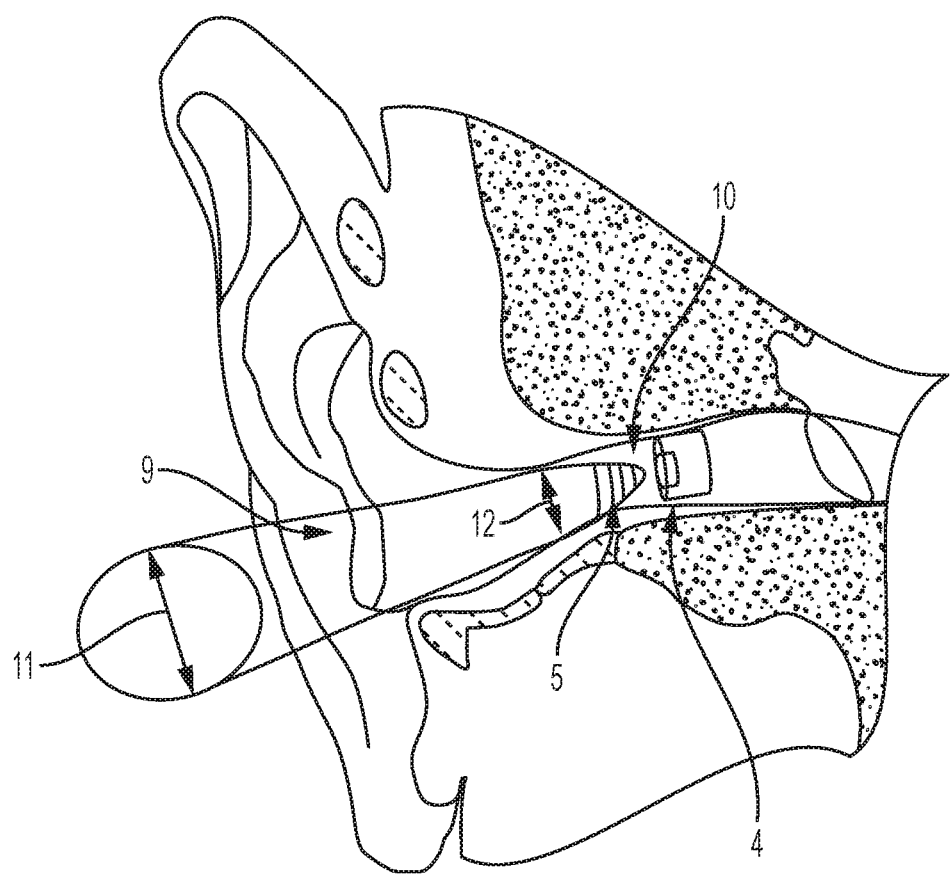
FIG. 3 depicts an apparatus containing a conical article for manipulation of an ear device.

In some instances, the apparatus can be a one piece continuous article. Referring to FIG. 2, the elongate section 1 and the stop section 2 can be the same component. In some cases, the combined elongate section 1 and stop section 2 can be a conical article. As depicted in FIG. 3, the apparatus can comprise a conical article 9 having a narrow end 10 and a wide end 11. In such a configuration, a portion 12 of the conical article 9 can have a diameter greater than a diameter of a subject's ear canal. This portion 12 of the conical article 9 could act to limit the insertion of the apparatus into the ear canal; thereby performing substantially the same function as the stop section 2 depicted in FIG. 2.

An elongate section 1 can be custom molded to fit a patient's ear canal. In other instances, a generic elongate section 1 can be used. The elongate section of the device that is manipulated into the ear canal can be at least about 2 mm, at least about 3 mm, at least about 4 mm, at least about 5 mm, at least about 6 mm, at least about 7 mm, at least about 8 mm, at least about 9 mm, at least about 10 mm, at least about 11 mm, at least about 12 mm, at least about 13 mm, at least about 14 mm, at least about 15 mm, at least about 16 mm, at least about 17 mm, at least about 18 mm, at least about 19 mm, at least about 20 mm, at least about 21 mm, at least about 22 mm, at least about 23 mm, at least about 24 mm, at least about 25 mm, at least about 26 mm, at least about 27 mm, at least about 28 mm, at least about 29 mm, at least about 30 mm, at least about 31 mm, at least about 32 mm, at least about 33 mm, at least about 34 mm, at least about 35 mm, at least about 36 mm, at least about 37 mm, at least about 38 mm, at least about 39 mm, at least about 40 mm, at least about 41 mm, at least about 42 mm, at least about 43 mm, at least about 44 mm, at least about 45 mm, at least about 46 mm, at least about 47 mm, at least about 48 mm, at least about 49 mm, or at least about 50 mm in length depending on the desired depth of insertion of the device. In some instances, the device that is manipulated into the ear canal can be at least about 1 cm, at least about 2 cm, at least about 3 cm, at least about 4 cm, at least about 5 cm, at least about 6 cm, at least about 7 cm, at least about 8 cm, at least about 9 cm, or at least about 10 cm in length.

An apparatus can be specifically configured depending on the application required. In some instances, an apparatus can be configured to fit into a right ear of a subject. In some instances, an apparatus can be configured to fit into a left ear of a subject. In some instances, an apparatus can be configured to fit into a right ear and a left ear of a subject. In some instances, an ear device in contact with the apparatus can be molded to specifically fit a subject's ear. In some instances, an ear device can be configured to adapt a general shape of an ear.

In some instances, the elongate section and the stop section can be the same component. An apparatus can be configured to fit into the conchal cavity of the ear and may be broadly convex or conical in form or shape. Thus, also disclosed herein are apparatuses comprising: (a) a conical article having a narrow end and a wide end; (b) an electromagnet associated with the narrow end of the conical article; where the electromagnet is magnetically attracted to a magnetic element associated with an ear device; and (c) a power source and a switch electronically connected to the electromagnet; where the switch turns the electromagnet on and off. For example, in some instances, the device can comprise a conical article having a narrow end and a wide end. In such a configuration, a portion of the conical article can have a diameter greater than a diameter of a subject's ear canal. This portion of the conical article could act to limit the insertion of the apparatus into the ear canal; thereby performing substantially the same function as the stop section.

In some instances, an apparatus can be comprised of separate, modular components that can be fastened or joined to each other. Examples of attachments that can be used to fasten or join components of the apparatus to one another can include a glue, an epoxy, a weld, a magnet, a screw, a ball bearing, a staple, a rivet, and any combination thereof. In some instances, the modular components of the apparatus can comprise low coefficients of friction at an attachment surface. In such a configuration, friction between the two surfaces can serve to fasten or join the components together.

In some situations, an elongate section 1 can be an arm for insertion into the canal of the subject. In some situations, a stop section 2 can be a flange designed to contact an outer ear of the subject when the elongate section 1 inserted into the ear of the subject, thereby preventing further insertion of the apparatus into the ear of the subject. In some instances, the flange can contact a pinna of a subject upon insertion of the elongate section 1. In some cases, the flange can further comprise a handle. In some cases, an elongate section 1 can be an arm and a stop section 2 can be a flange.

In some cases, the apparatus may be formed from a resilient and compliant material. Components of the apparatus can be flexible, flexible, or rigid depending upon the material used to construct the apparatus. In some instances, the apparatus can be composed at least in part of a material selected from the group consisting of a plastic, a silicon, a wood, a metal, a rubber, a thermoplastic polyurethane, a graphene, an aluminum mesh, a stone, a titanium compound, a paper, a marble, a cloth, a carbon fiber, a wax, gold, silver, platinum, palladium, tungsten, stainless steel, a jewel, and any combination thereof. In some instances, a plaster or similar moldable material can be used to construct an apparatus that can be custom molded to the ear canal of the subject. Materials comprising at least the external surfaces of the apparatus can be non-allergenic, medical grade, and biocompatible.

Figure 4:
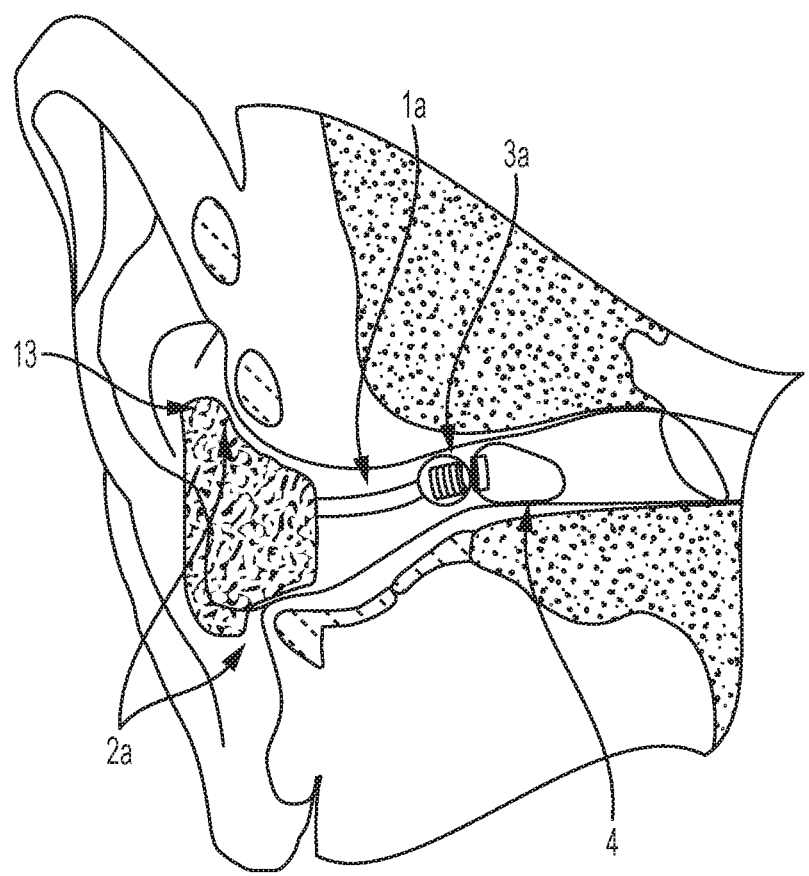
FIG. 4 depicts an embodiment of an apparatus described herein which contains a flexible arm component.

Referring now to FIG. 4, an apparatus 13 can comprise flanges 2a and a flexible elongate section 1a sufficient to navigate the ear canal of the subject upon insertion. In some cases, the apparatus 13 can be used for insertion, removal or manipulation of an ear device 4 though association with a magnet 3a, which can be optionally wrapped in a soft material to prevent laceration of the ear canal.

In some instances, an apparatus described herein can be wholly or partly biodegradable or recyclable. In some instances, individual modular components of the device can be composed at least in part of recyclable or a biodegradable material. In some instances an elongate section 1 can be at least partially biodegradable. In some instances, the elongate section 1 is at least about 1%, 5%, 10%, 15%, 20%, 25%, 30%, 35%, 40%, 45%, 50%, 55%, 60%, 65%, 70%, 75%, 80%, 85%, 90%, 95%, or about 100% recyclable. In some instances, the elongate section 1 is at least about 1%, 5%, 10%, 15%, 20%, 25%, 30%, 35%, 40%, 45%, 50%, 55%, 60%, 65%, 70%, 75%, 80%, 85%, 90%, 95%, or about 100% biodegradable. In some instances, the stop section 2 is at least about 1%, 5%, 10%, 15%, 20%, 25%, 30%, 35%, 40%, 45%, 50%, 55%, 60%, 65%, 70%, 75%, 80%, 85%, 90%, 95%, or about 100% recyclable. In some instances, the stop section 2 is at least about 1%, 5%, 10%, 15%, 20%, 25%, 30%, 35%, 40%, 45%, 50%, 55%, 60%, 65%, 70%, 75%, 80%, 85%, 90%, 95%, or about 100% biodegradable. In some instances, the conical article 9 is at least about 1%, 5%, 10%, 15%, 20%, 25%, 30%, 35%, 40%, 45%, 50%, 55%, 60%, 65%, 70%, 75%, 80%, 85%, 90%, 95%, or about 100% recyclable. In some instances, the conical article 9 is at least about 1%, 5%, 10%, 15%, 20%, 25%, 30%, 35%, 40%, 45%, 50%, 55%, 60%, 65%, 70%, 75%, 80%, 85%, 90%, 95%, or about 100% biodegradable.

In some instances, an apparatus described herein can be wholly or partly reusable. In some cases, a portion of a device can be separated from the remainder of the apparatus for disposal while the remainder of the device is retained for further use. In some instances, a disposal probe or tip can be fastened to the magnet 5 in order to reuse the device without the need for sterilization. In some instances, the stop portion 2 can be separated and disposed of while the remainder of the device can be retained for further use. In some instances, a device can be at least partially collapsible to facilitate transport or storage of the apparatus when not in use. In some instances, an apparatus or a component of the apparatus has a length of at most about 3 cm, at most about 2.5 cm, at most about 2 cm, at most about 1.5 cm, at most about 1 cm, at most about 0.5 cm, at most about 0.4 cm, at most about 0.3 cm, at most about 0.2 cm, at most about 0.1 cm, or at most about 0.05 cm when at least partially collapsed.

An apparatus described herein may further comprise additional modification to perform additional functions. For instance, the apparatus may comprise a light or camera to be used to visualize the ear canal of the subject upon insertion of the apparatus. An apparatus can be constructed employing a visualization means by inserting, for example, a fiber optic light or camera through an aperture in the proximal end of the apparatus and threading said visualization means through the housing of the apparatus and out an aperture on the distal end of the apparatus. The addition of apertures to incorporate visualization means, as well as the incorporation of the visualization means through the apparatus, is well within the skill of a practitioner in the art.

Magnet

An apparatus described herein can contain a housing, which can have an elongate section 1 that is introduced into the ear canal (see e.g. FIG. 2). The apparatus can have a magnet (electrically inducible or permanent magnet) that can be present on a distal end of the elongated section, or can be moved to the distal end of the elongate section.

An apparatus described herein can have a magnet that is not inducible as the electromagnet, for instance, the magnet can be a static magnet (permanent magnet). In some embodiments, the apparatus can be configured to hold the ear device via at least a magnetic attraction between the magnet and the magnetic element of the ear device during the insertion of the apparatus into the ear, thereby inserting the ear device into the ear. The ear device can be appropriately sized to the ear of the subject. The size of the ear device can be configured in a way that when the ear device is inserted in the ear at a predetermined position, the friction between the ear device and the ear canal can be relatively large, so that when the apparatus is being removed from the ear, the magnetic attraction is unable to overcome the friction. In another word, the friction between the ear and the ear device can overcome the magnetic attraction, consequentially detaching the ear device from the apparatus that is being removed from the ear. As a result, the ear device can be inserted into the ear and retained at the predetermined position by using the apparatus having the static magnet, in some cases, without the need of activating and deactivating the electromagnet.

Figure 5:
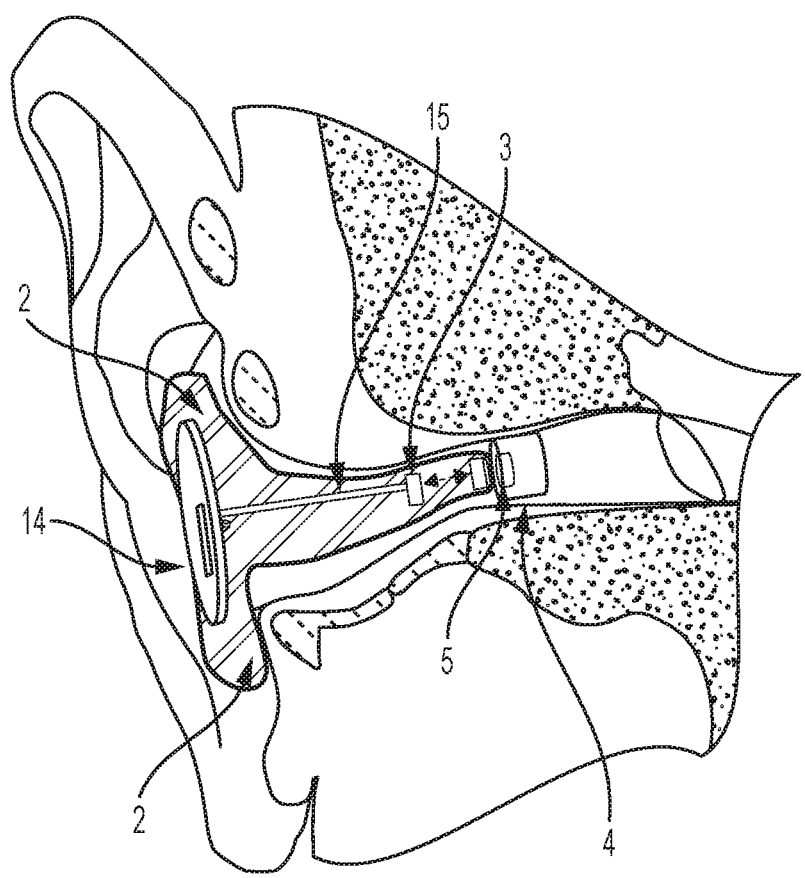
FIG. 5 depicts an embodiment of an apparatus described herein containing a mechanical actuator to modulate the position of the magnet.

Referring to FIG. 5, an apparatus can contain a mechanical means 15 to produce a translation of the translatable magnet 16 through mechanical actuation of a mechanical actuator 14. In some cases, the mechanical means can be a pulley, a string, a rubber or elastic band, a fiber, or a combination thereof. In some instances, the mechanical means 15 does not comprise a pin, a metal rod, a spring, or a combination thereof disposed in the elongated section.

Figure 6:
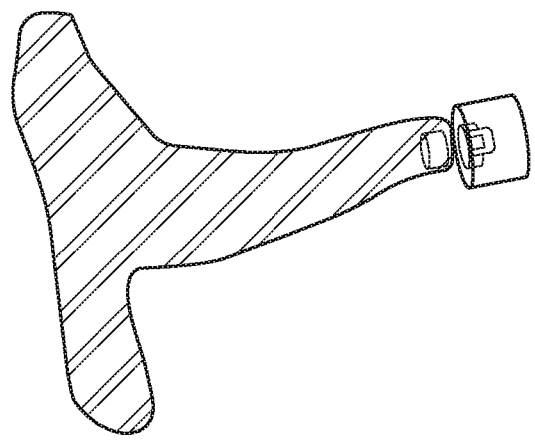
FIG. 6 depicts an embodiment of an apparatus described herein which can be used to rotate an ear device within the ear of a subject.

The activity of the magnet at the distal end can be turned on or off, or polarity reversed by electric means, or by physical movement or rotation of the magnet (see e.g. FIG. 6).

Figure 7:
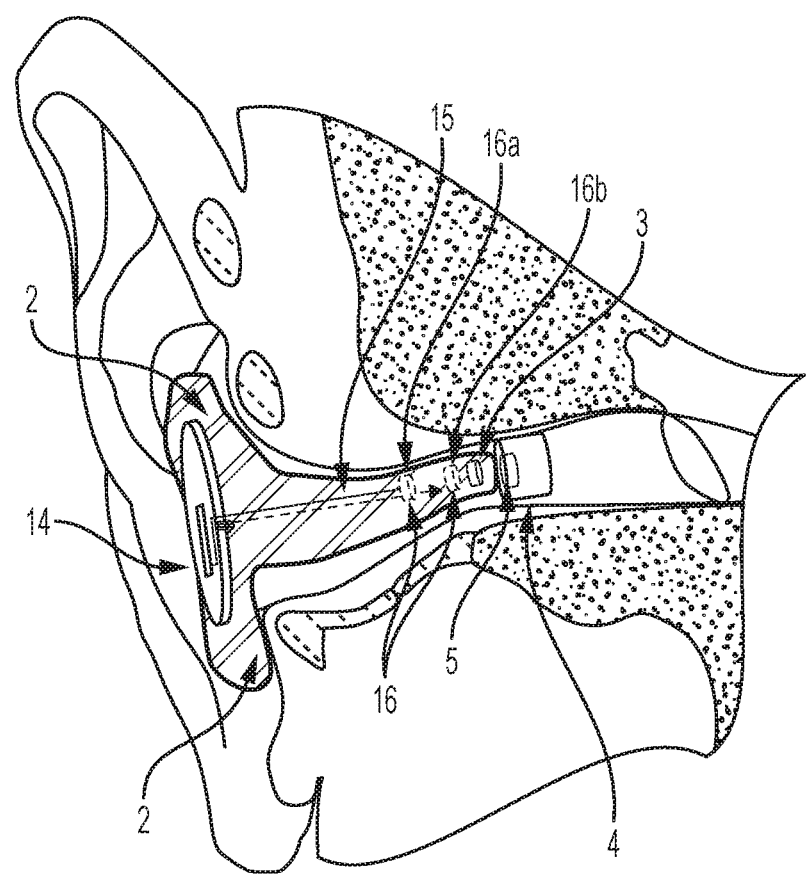
FIG. 7 depicts an apparatus which comprises a pair of magnets.
Figure 8:
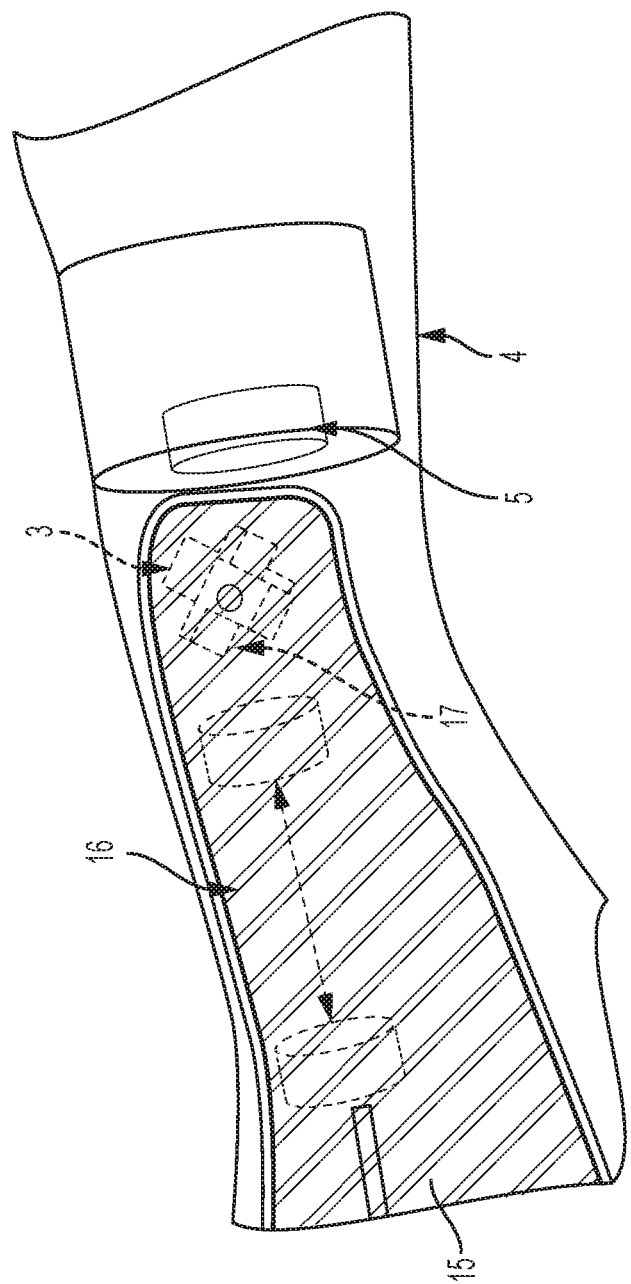
FIG. 8 depicts a rotation of a distal magnet through mechanical actuation of a translatable magnet.

In some cases, an apparatus can have a plurality of magnets. In some instances, a magnet 3 localized on a distal end of an apparatus as depicted in FIG. 2 can be combined with a translatable magnet 16 as depicted in FIG. 5 to produce a magnet containing dual magnets as depicted in FIG. 7. In such a configuration, the mechanical switch 14 can be actuated to result in a translation of translatable magnet 16 from a proximal position 16a to a distal position 16b via mechanical means 15 in the direction of the magnet 3 localized on the distal end of the apparatus. Translation of the translatable magnet 16 towards the localized magnet 3 can be used to manipulate the localized magnet 3, thereby manipulating an ear device 4 that is magnetically attracted thereto. For instance, the localized magnet 3 can be fixed to the distal end by a fastening means (e.g. rod 17) that can allow for rotation of the magnet 3 along an axis. Such rotation can occur when the polarity of the translatable magnet 16 is the same as that of magnet 3, such that proximity of translatable magnet 16 can cause a rotation of magnet 3 through magnetic repulsion. Such rotation can be used to further manipulate eat device 4 in the ear canal. For example, a rotation of magnet 3 can cause a repulsion between magnet 3 and a magnetic element 5 of ear device 4, which can result in further insertion of the ear device 5 into the ear canal. Furthermore, a combined embodiment as depicted in FIG. 7 can comprise both an electrical and mechanical actuation mechanism. For example, the translatable magnet 16 can be an electromagnet electronically connected to a power source 6 (see e.g. FIG. 2) by a wire, which can be attached to the mechanical means 15 such that the translatable magnet 16 can be translated distally and/or electronically actuated. Such actuation can lead to the option to modulate the polarity of translatable magnet 16, which can be used to precisely rotate magnet 3 along rod 17, and thereby manipulate ear device 4 within the ear canal in a controlled manner. For example, precise rotation of magnet 3 through electronic actuation of translatable magnet 17 can be used to orient an ear device after insertion without having to remove the ear device.

It is also envisaged that such fine control of orientation can be performed through the use of an array of electromagnets. Such an array can be constructed along the distal end of the elongated section 1 in sequence. In such a configuration, switch 7 can be in the form of a touch screen or other input/output device to allow precise control of individual electromagnets in order to perform precise manipulations of the ear device within the ear. In some cases, individual magnets in the array can be actuated sequentially, while in other cases the array could be actuated all at once.

When the magnet is activated at the distal end, it will engage with a magnetic material on a device to be inserted in the ear canal. In some instances, the surface area of the ear device can be comprised at least in part of the magnetic material. In some cases, the surface area comprising a magnet can be at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the total surface area of the ear device. In some cases, the ear device can be comprised entirely of a magnetic material.

In some instances, the apparatus can be comprised at least in part of the magnetic material. In some cases, the surface area of the apparatus comprising a magnet can be at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the total surface area of the apparatus. In some cases, the apparatus can be comprised entirely of a magnetic material.

Figure 10:
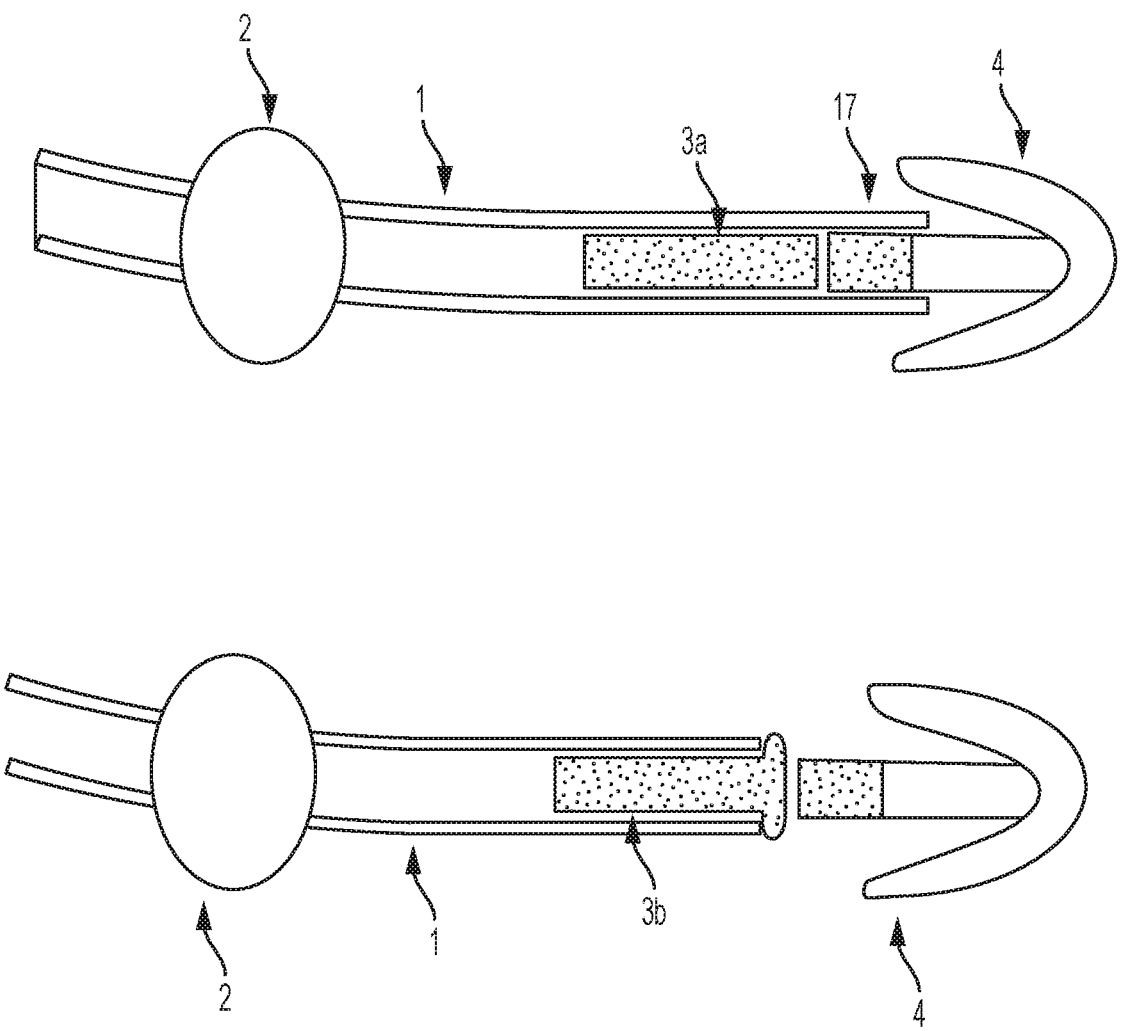
FIG. 10 depicts an apparatus containing an orientation restriction section and an apparatus that does not contain an orientation restriction section.

In some instances, the apparatus can comprise an orientation restriction section. The orientation restriction section can be configured to maintain the orientation of the ear device consistent with the orientation of the insertion apparatus during insertion of the ear device into the ear. The orientation restriction section can restrict the orientation of the ear device at least in part by mechanical force, electrostatic force, magnetic force, or any combination thereof. FIG. 10 depicts an exemplary apparatus comprising an orientation restriction section. The upper apparatus in the figure comprises an elongated section 1, a stop section 2, an orientation restriction section 17, and a magnet 3a. The orientation restriction section 17 in this case is an offset from the magnet end of the apparatus. It is a hollow tubule in structure. As shown in the figure, a portion of the ear device is inserted into the orientation restriction section 17. When it is appropriately sized, the orientation restriction section 17 can constrain at least a portion of the ear device inside its hollow tube structure, limiting the lateral movement when the ear device is being inserted into the ear, thereby preventing change in the orientation of the ear device. It should be noted that the orientation restriction section can be of any form as long as it maintains the orientation of the ear device consistent with the orientation of the insertion apparatus during insertion of the ear device into the ear. For instance, it can comprise a clamp, a partially or completely enclosed hollow structure, or both.

Examples of ferromagnetic materials can comprise at least one of alnico, bismanol, chromium (IV) oxide, cobalt, a complex oxide, dysprosium, fernico, ferrite (iron), ferrite (magnet), gadolinium, gallium manganese arsenide, a heusler compound, iron, KS Steel, magnadur, a magnetic semiconductor, magnetite, Metglas, MKM steel, a neodymium magnet, nickel, permalloy, a rare-earth magnet, a samarium-cobalt magnet, Sendust, Suessite, or a Yttrium iron garnet.

In some cases, a magnet can have a predetermined magnetic field strength. In some cases, a magnet can have a variable magnetic field strength. In some cases, a magnet can have a magnetic field strength of about 0.05, 0.051, 0.052, 0.053, 0.054, 0.055, 0.056, 0.057, 0.058, 0.059, 0.06, 0.061, 0.062, 0.063, 0.064, 0.065, 0.066, 0.067, 0.068, 0.069, 0.07, 0.071, 0.072, 0.073, 0.074, 0.075, 0.076, 0.077, 0.078, 0.079, 0.08, 0.081, 0.082, 0.083, 0.084, 0.085, 0.086, 0.087, 0.088, 0.089, 0.09, 0.091, 0.092, 0.093, 0.094, 0.095, 0.096, 0.097, 0.098, 0.099, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, or 1 Tesla.

IV. Ear Devices

An apparatus described herein can be used in conjunction with a wide array of ear devices that can be employed for various functions. While the figures provided herein depict an ear device of generally discoidal shape, the choice of ear device is not limited by this depiction. In some cases, an ear device described herein can be in communication with other devices, whether internal or external, in order to transmit data such as a result to the other device. In some cases, an ear device can comprise a storage medium to store information such as a hard drive, flash memory, etc. In some situations, an ear device described herein can upload data to cloud storage. Specific non-limiting examples of ear devices compatible with an apparatus described herein are discussed below in greater detail.

Earplugs

In some instances, an ear device can be an earplug. In some instances, the ear plug can be comprised of a pliable material such as foam or rubber that can be compressed to a diameter less than the diameter of a portion of the subject's ear canal.

Insertion of foam earplugs as described in the art typically can comprise squeezing the earplug to decrease its diameter, placing the ear plug in the ear canal, and having it expand to occlude the ear canal. For this reason, foam earplugs may be generally designed longer than is acoustically needed, which can allow the ear plug to be manipulated from the outer portion of the subject's ear after insertion, and removed as needed. One problem most earplugs in the art encounter is that, after insertion, they can be extruded out of the ear canal as they expand, thereby breaking the acoustic seal.

The use of an apparatus as described herein can be used in tandem with an earplug in order to insert the ear plug deep into the ear canal of the subject, thereby preventing extrusion of the earplug from the ear canal. An earplug can comprise a magnetic element that can be magnetically attracted to the magnet 3 of the apparatus, thereby allowing for insertion, removal or other manipulation of the earplug in the ear of the subject.

In some instances, an earplug compatible with an apparatus described herein can be used in a variety of situations. For example, an earplug can be inserted deep into the ear canal in order to at least partially regulate sound waves transmitted into the ear canal of the subject. The composition of the earplug can be adjusted to modulate the acoustics of the ear plugs to allow for greater or fewer sound waves transmitted into the ear after insertion. Another example can include regulation of pressure transmitted into the ear of the subject. The applicability of such an earplug could include situations that result in increased pressure being applied to the ear, such as deep diving or air flights. Again, the composition of the earplug can be adjusted to modulate the amount of pressure transmitted into the ear after insertion.

Communication Devices

In some instances, an ear device can be a communication device. Examples of communication devices can include recording devices, transmission devices, receiving devices, translation devices, and authentication devices.

Recording devices could be used, for example in recording situations for later consumption such classroom lectures, concerts, speeches, or important conversations.

Potential use of transmission device could include transmitting a location from a wearer. In some situations, this could be used in reconnaissance missions, as law enforcement or military personnel could transmit a position to their colleagues in real time without the fear of discovery of the device. Another example of use of such a transmission device could include inserting the ear device into the ear of an individual sentenced to house arrest. This device could be used as an alternative to ankle bracelets currently in use, with the advantage of being less cumbersome and potentially increasing compliance from the subject.

Further use of receiving devices can include replacement of cumbersome headsets and ear buds to listen to conversations, phone calls, directions, music, and other media. For example, an ear device capable of receiving transmission can be used by news casters as an alternative to the ear devices currently in use, which would allow the same functionality while concealing the device within the ear canal. An ear device concealed in the ear could also be used as an alternative to ear phones that can be in communication with a smartphone or other device capable of transmitting media to the ear device such as a radio or mp3 player. As the ear device is placed within the ear canal, loss of the ear device could be mitigated relative to existing ear phones which can easily fall out of the ear.

Devices capable of recoding, transmission and receiving could be used in situations in which covert placement of a recording device could be beneficial. For example, an ear device capable of transmission and receiving could be used as an alternative to the use of wires in law enforcement or special operations. As the ear device could be placed deep within the ear canal and away from sight, a law enforcement individual could be protected from discovery of the device. The ability to transmit instructions directly to the ear canal could also be used in similar situations. Because the instructions would be delivered to the ear canal of the wearer, the instructions could be isolated to the subject without fear of others being able to hear the instructions.

Another example of a communication device compatible with an apparatus described herein is a translation device. Examples translation ear devices can be found, for instance, in U.S. Pat. Nos. 8,527,280, 7,676,372, and US20030065504. Insertion of such a device deep within the ear canal using an apparatus described herein would be advantageous over existing translation devices in that they would be concealed within the ear. This concealment could allow for rapid translation of the foreign language to the subject without the knowledge by the person communicating to the user that a translator is in use. This could result in a more natural exchange between the user and the person they are communicating with.

It is also possible to combine a transmission device with an earplug as previously described to produce a device that employs transmission of destructive interference into the ear canal to minimize sound waves transmitted into the ear of the subject after insertion using a device described herein. Such a device can include a noise canceling element capable of transmitting the destructive interference that can be imbedded in a foam ear plug to be inserted into the ear canal. In some instances, the apparatus upon actuation can be used to turn the noise canceling element on or off when the device is in contact with the ear device. In other instances, it is possible to modulate the noise canceling element using an external device in communication with the ear device such as a laptop computer or a smartphone.

Authentication Devices

In some instances, an ear device compatible with an apparatus described herein can be a device used for authentication. In some instances, the authentication device can act as a means, be it primary or in combination with other means such as passwords, biometric, etc, to provide access.

For example, an ear device can be inserted into the ear canal that can act as a key fob. This could allow the subject to access, for instance, controlled access areas simply by approaching the controlled access point without needing to produce a separate access device such as a card or key. This would potentially ameliorate loss of access privileges by minimizing loss of access credentials due to the retention of the key fob within the ear of the subject.

Another example could be the use of a device that acts as an access token through electronic transmission between the ear device and a device requiring authentication. Such control could be used in tandem with a password to produce additional layers of security and minimize the risk of outside intrusion.

Medical Devices

In some instances, an ear device compatible with an apparatus described herein can be a medical device. Examples of medical devices can include hearing aids, diagnostic devices, and devices capable of treatment to the subject.

Hearing aids can include deep in ear canal (DIC) hearing aids, examples of which are disclosed in U.S. patent application Ser. No. 12/841,120. DIC hearing aids comprising magnetic elements can be inserted into the ear of the subject through an apparatus described herein, either by the subject directly or another individual. An apparatus described herein can further be used to actuate (i.e. power on or off) the DIC hearing aid when in contact with the ear device. Furthermore, an apparatus described herein can be used to manipulate the placement/orientation of the hearing aid through manipulation of the magnet attached to the distal end of the apparatus as described above.

In some cases, a device placed within the ear canal of the subject can be used to monitor signals corresponding to various vital signs in the subject. For example, an ear device can be an electroencephalogram (EEG) monitoring device. Examples of such devices compatible for ear placement can be found in US 20110004089. Such a device can be used to detect electrical signals in the brain of the subject, which can be used to diagnose disorder such as sleep disorders such as sleep apnea; brain trauma; and neurodegenerative diseases such as Alzheimer's disease, schizophrenia, and Parkinson's disease.

Another example of a diagnostic device can include a device capable of monitoring cardiovascular parameters of a subject within the ear canal such as pulse, dissolved oxygen level, blood pressure, etc. Examples of such devices can include ear oximeters as described in U.S. Pat. Nos. 3,412,729 and 2,706,927. Such a device can be used to determine a likelihood of a cardiovascular disease such as a stroke or heart attack in real time from within the ear canal. The result can then be communicated to an external device and used to guide potential treatment by a healthcare professional.

A diagnostic device can further comprise means to measure and record other vital signs when placed in the ear of the subject. For example, a thermometer can be appended to an ear device to measure an electrical signal corresponding to a body temperature of the subject. In another embodiment, an ear device can detect signals that correlate to species in circulation in a blood vessel. For instance, a device can monitor a salinity level, a dissolved oxygen level, or a glucose level in a blood vessel.

It is also possible to insert a device for ameliorating a condition or disease using an apparatus as described herein. For instance, the use of a device that transmits destructive interference as described above can be used to at least partially ameliorate an ear condition such as tinnitus that has been shown to be treatable through the use of listening devices (see e.g. US Publication No. 20120308060). Furthermore, a magnetic field generator can be incorporated into an ear device such that, when actuated, a disorder can be partially ameliorated. Examples of such disorders can include a migraine; a loss of taste; a loss of smell; Parkinson disease; a depression disorder; major depression disorder; and any combination thereof.

Other Ear Devices

It is possible to insert means for displaying non-piercing jewelry using an apparatus as described herein. For instance, an ear device can comprise jewelry that can be visible from the outside of the ear canal upon insertion using the apparatus.

Alternatively, it is possible to insert a magnet into the inner ear using the apparatus. The magnet, when inserted into the inner ear, could be used to attract objects containing magnetic elements, and thereby stabilize them on the outer ear of the subject. For example, a piece of jewelry such as an earring can be stabilized on the outer ear through magnetic attraction without the need for additional piercings. Additionally, objects such as magnetic headphones (see e.g. US Pub No. 20150195639) can be stabilized on the outer ear of the subject though magnetic attraction to the magnet placed in the ear canal, thereby minimizing loss of the magnetic earphone from falling from the outer ear.

An ear device may also be coated in a disposable material such as a cloth or cotton to be sued to remove ear wax from an ear. In such a configuration, a magnetic element can be wrapped in the disposable material similar to the magnet $3a$ depicted in FIG. 4. This ear device can be inserted using an apparatus described herein, and can be subsequently rotated within the ear canal of the subject, thereby collecting and removing excess wax from the ear canal.

V. Methods of Use

Also disclosed herein are methods of using an apparatus described herein to manipulate an ear device described herein within the ear canal of a subject.

In some instances, the method can comprise inserting an ear device comprising a magnetic element into the ear of the subject comprising inserting an apparatus described herein into the ear of the subject, where the apparatus is in contact with the magnetic element of the ear device through a magnetic attraction. To introduce the ear device into the ear, the magnet of the apparatus can be activated to produce a magnetic attraction between the ear device and the magnet of the apparatus. The elongate section of the apparatus can be introduced along with the ear device into the ear canal. In some instances, a flange on a proximal end of the device can contact an outer ear of a subject, and thereby prevent over insertion of the elongate section into the ear canal. When fully inserted, the activity of the magnet within the housing can be released, thereby removing the magnetic attraction between the apparatus and the ear device. In some cases where the magnet is an electromagnet, the activity of the magnet is released through activating a switch on the apparatus, thereby electrically powering off the magnet. In some cases, a device with a mechanical actuator such as depicted in FIG. 5 can be actuated to mechanically disengage the magnet from the ear device. In some instances, the apparatus can then be removed, while the ear device remains in the position deep in the ear canal.

In some embodiments, the ear device comprising a magnetic element can be manipulated by apparatuses that comprise a non-inducible permanent magnet. In some cases, the manipulation can comprise insertion of the ear device into an ear of a subject using an insertion apparatus. The insertion apparatus can comprise an elongated section; a stop section associated with the elongated section; and a magnet associated with a first end of the elongated section. The stop section can contact a portion of an ear of a subject when the elongated section is inserted into an ear of the subject, thereby preventing further insertion of the elongated section into the ear of the subject. The magnet can be a permanent magnet. The magnet can be configured to be magnetically attracted to the magnetic element of the ear device. The insertion apparatus can be configured to hold the ear device during its insertion into the ear via at least a magnetic attraction between the magnet and the magnetic element of the ear device, thereby inserting the ear device into the ear. In some cases, after the ear device is inserted into a predetermined position of the ear of the subject, the insertion apparatus can be removed from the ear, leaving the ear device retained at the predetermined position. In these cases, the ear device can be appropriately sized to the ear of the subject, such that when the ear device is inserted at the predetermined position and the insertion apparatus is being removed from the ear, a friction between the ear and the ear device can overcome the magnetic attraction to detach the ear device from the apparatus, thereby retaining the ear device at the predetermined position.

In some embodiments, the manipulation of the ear device can comprise removal of the ear device from the predetermined position in the ear using a removal apparatus. The removal apparatus can comprise an elongated section and a magnet associated with a first end of the elongated section. The magnet can be a static magnet. To remove the ear device from the predetermined position in the ear, one can insert the removal apparatus into the ear in such a manner to produce a magnetic attraction between the magnet of the removal apparatus and the ear device, and then remove the removal apparatus. In these cases, the magnet can be configured to be magnetically attracted to the magnetic element of the device. After insertion, the removal apparatus can be configured to hold the ear device during its removal from the ear via at least a magnetic attraction between the removal apparatus and the magnetic element of the device. In some situations, the magnetic attraction can overcome the friction, thereby pulling the ear device out of the ear when the apparatus is being removed from the ear.

In some situations, the polarity of the magnet may be reversed (either electrically, or by mechanical rotation of a permanent magnet, or by translation of another oppositely oriented magnet). This will allow for physical repulsion of an ear device containing a magnet element, and thereby further insertion of the ear device deep in the ear canal beyond the physical reach of the arm of the insertion device.

In some situations, the insertion of the ear device into the ear canal results in a concealment of the ear device within the ear canal such that the ear device is not visible from the outside of the ear. Thus, in some situations, the method of insertion can be a method of concealing objects within the ear canal.

In some instances, a method can comprise removing an ear device comprising a magnetic element from the ear of the subject comprising inserting an apparatus described herein into the ear of the subject. As described with respect to the insertion, the elongate section of the apparatus can be introduced along with the ear device into the ear canal. When fully inserted, the activity of the magnet within the housing can be positively actuated, thereby producing a magnetic attraction between the apparatus and the ear device. In some cases where the magnet is an electromagnet, the activity of the magnet is powered on through activating a switch on the apparatus, thereby electrically powering on the magnet. In some cases, a device with a mechanical actuator such as depicted in FIG. 5 can be actuated to mechanically engage the magnet from the ear device. In some cases, the magnet is positively activated prior to the insertion of the apparatus into the ear canal. Once the ear device is engaged with the magnet on the distal end of the apparatus, the apparatus can be removed from the ear canal, thereby removing the ear device from the ear of the subject.

As described above, an ear device can have a magnetic element that can engage with the magnet of an apparatus described herein. Referring to FIG. 2, the magnetic element 5 on the ear device can be a ferromagnetic element that will be attracted to the magnet 3 on the distal end of the apparatus. In some instances, the magnetic element 5 can be a ferrimagnetic element. In some instances, the magnetic element 5 can be an antiferromagnetic element. The magnetic element 5 of the ear device may have a specific polarity and orientation. Further, it may also contain an array of magnets which can allow engagement and attraction to a magnet of the apparatus in a specified orientation. This will allow specification of the rotational orientation of the ECO within the ear canal. Thus, a method can comprise: (a) inserting an apparatus described herein into the ear of the subject; (b) activating an electromagnet; thereby providing a magnetic attraction between the magnetic element of the ear device and the electromagnet; and (c) manipulating the apparatus; thereby manipulating the ear device in the ear of the subject. Such a manipulation can comprise manipulation of depth such as distally or proximally translating the ear device within the ear canal, manipulation of orientation of the ear device, or rotation of the ear device within the ear canal.

Figure 9:
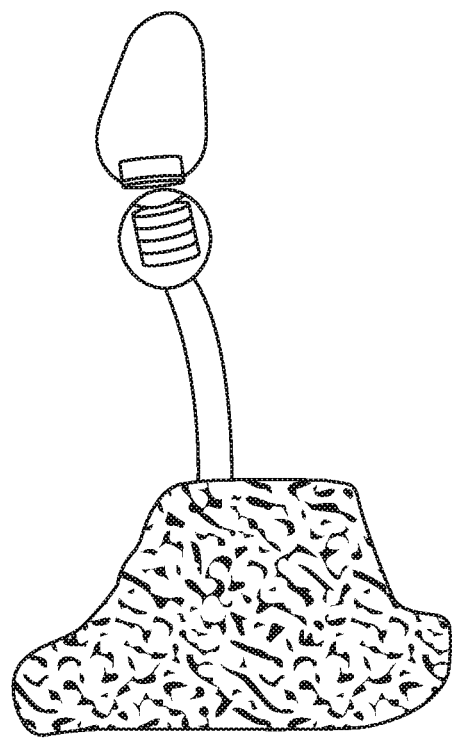
FIG. 9 depicts a pair of devices in which an insertion device without a magnetic means is used to insert an ear device while a retrieval device containing a magnetic means is used to retrieve the ear device.
Figure 9:
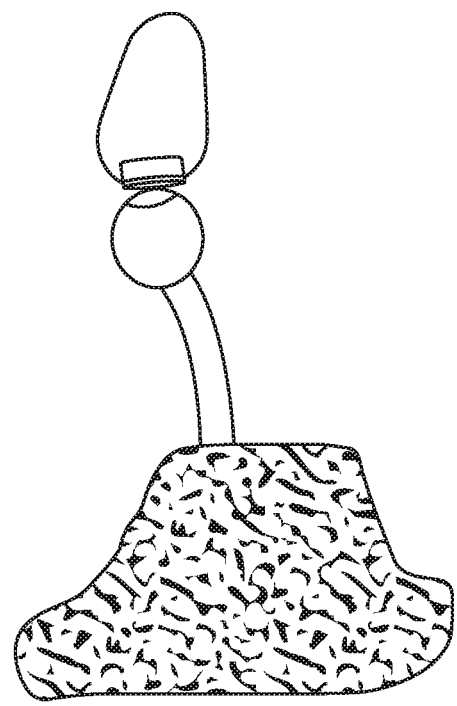

It is also possible to employ a plurality of apparatuses for different uses. For example, as depicted in FIG. 9, an insertion apparatus may be used to insert an ear device that does not contain a magnet. Rather, the insertion device can be used to insert the ear device mechanically rather than through magnetic attraction. To remove the ear device, a retrieval apparatus comprising a fixed magnet can be used that is separate and distinct from the insertion device.

In some embodiments, the ear device comprises a linker, and the magnetic element is associated with the ear device through the linker. In some cases, the linker can be elongatable, like a spring made of any type of materials (e.g., metal, plastic), or an elastomer. In some cases, the linker is not elongatable, but it can switch from a resting loose state and an extended tight state. In some cases, it can be a soft string. The soft string can be made of cotton, pulp, linen, bamboo, kenaf, silk wool, viscose rayon, copra, lyocell, polyethylene, polypropylene, polyethylene terephthalate, polybutyrene terephthalate, nylon, polyacrylic, or any combination thereof. As shown in FIG. 11, the ear device comprises a magnetic element 5, as well as a linker 18 that associates the magnetic element 5 to the main body of the ear device 19. The figure depicts an exemplary process of manipulating the ear device from an ear using exemplary apparatuses as disclosed herein. In panel (a), the apparatus comprises an elongated section 1, a stop section 2, and a magnet 3a, which, for instance, can be used to insert the ear device into an ear, or any other of movement/transportation of the ear device. In panels (b) and (c), both of the apparatuses comprise an elongated section 1, a stop section 2, and a magnet 3b. In panel (c), the bottom apparatus contacts the magnetic element 5 of the ear device and pulls it so that the linker 18 can be extended to be longer than a resting state as depicted in panels (a) and (b). In some cases, the removal of the ear device from an ear of a subject can comprise: removing the apparatus until at least a portion of the linker is extended to outside of the ear; and pulling the linker to remove the ear device.

VI. Manufacturing

Also disclosed herein are methods of manufacturing an apparatus as described herein. In some instances, an apparatus described herein can be assembled from modular components that can be attached together to form an apparatus. For example, a method of manufacturing an apparatus can comprise: (a) attaching an electromagnet to a first end of an elongated section of the apparatus; and (b) electrically connecting a power source and a switch to the electromagnet, where the switch turns the electromagnet on and off. In some cases, a stop section such as a flange can be attached to a second or proximal end of the apparatus, where the stop section contacts a portion of an ear of a subject when the elongated section is inserted into the ear of the subject, thereby preventing further insertion of the elongated section into the ear of the subject.

In some embodiments, the apparatus can be molded plastic. An apparatus can comprise an elastomer body with various features to aid in the process of placing the earplug and retrieving the earplug. The apparatus can include safety features and features to aid the user during use.

In some embodiments, the apparatus can comprise thermoplastic, liquid silicone rubber (LSR), thermoplastic elastomers (TPE), or a thermoplastic polyurethane (TPU) parts. In certain non-limiting embodiments, these parts could be machined, injection molded, cast, sintered, and/or 3D printed.

In certain cases, the electromagnet can be made of a metal coil through which electricity is run through to generate the magnetic field. The coil could be of any gauge size. In some embodiments, the coil can be between 12 to 36 gauge. In certain cases, the coil can be made of conductive material, for instance, copper. In some embodiments, the coil can have a protective coating. In certain cases, the coating can be an enamel.

In some embodiments, the apparatus can have sections to control the heat generated by the electromagnet when the electricity is passing through. In certain circumstances, this can involve an active cooling feature, like a fan or heat sink.

Also disclosed herein are methods of manufacturing certain ear devices as described in the present disclosure.

In some embodiments, the ear device can be an elastomer or an elastomeric material overmolded on a ferritic or magnetic material (permanent magnet) and a portion of the ferritic or magnetic material can be exposed out of the elastomer.

In some embodiments, the elastomer can be liquid silicone rubber (LSR), thermoplastic elastomers (TPE), or a thermoplastic polyurethane (TPU). In certain cases, the elastomer can comprise a hardness as determined by a durometer. In some cases, an elastomer can be comprise a durometer hardness of from 5 to 100 shore A, from 10 to 100 shore A, from 15 to 100 shore A, from 20 to 100 shore A, from 25 to 100 shore A, from 30 to 100 shore A, from 35 to 100 shore A, from 40 to 100 shore A, from 45 to 100 shore A, from 50 to 100 shore A, from 55 to 100 shore A, from 60 to 100 shore A, from 70 to 100 shore A, from 75 to 100 shore A, from 80 to 100 shore A, from 85 to 100 shore A, from 90 to 100 shore A, from 95 to 100 shore A, from 10 to 80 shore A, from 20 to 80 shore A, from 30 to 80 shore A, from 40 to 80 shore A, from 50 to 80 shore A, from 60 to 80 shore A, or from 70 to 80 shore A. In some cases, an elastomer can be comprise a durometer hardness of about 5 shore A, about 10 shore A, about 15 shore A, about 20 shore A, about 25 shore A, about 30 shore A, about 35 shore A, about 40 shore A, about 45 shore A, about 50 shore A, about 55 shore A, about 60 shore A, about 65 shore A, about 70 shore A, about 75 shore A, about 80 shore A, about 85 shore A, about 90 shore A, about 95 shore A, or about 100 shore A.

A ferritic or magnetic material can be manufactured by a grinding, machining, casting, or sintering process. In certain cases, the ferritic or magnetic material may also have a coating to protect from corrosion. The coating may be an electroplating (typically nickel), a powder coating, or a porcelain enamel coating. In certain cases, the ferritic or magnetic material may be placed in the elastomer tool and the elastomer can be injected around it (i.e. overmolding). The ferritic or magnetic material can have features, geometric and surface, to help retain the elastomer. The features may include, but not limited to, undercuts, jogs, holes, and texture. In certain cases, multiple plugs can be overmolded on a single continuous piece of the ferritic or magnetic material. Post the overmolding process the piece of the ferritic or magnetic material can be cut into sections where each resultant section may become an individual plug. In these exemplary cases, the ferritic or magnetic material itself may need to be corrosion resistant and biocompatible or a secondary coating may need to be applied to the cut ends.

In some embodiments, the earplug can be an elastomeric material overmolded on a ferritic or magnetic material and a portion of the ferritic or magnetic material is not exposed out of the elastomer. In these embodiments, the ferritic or magnetic material may not have a corrosion resistant coating since the elastomer can be the coating to protect it.

In some embodiments, the earplug can be an injection molded elastomeric material and a ferritic or magnetic material can be inserted in the elastomer post the elastomer molding. In these embodiments, the elastomer may be molded with a cavity that the ferritic or magnetic material can be inserted into. In certain cases, the cavity can be expanded or stretched to provide better access to the ferritic or magnetic material and to aid in retention.

VII. Kits

Also disclosed herein are kits, comprising an apparatus described herein and instructions for use. These kits can be assembled in suitable packaging for shipment and storage of the apparatus. Furthermore, a kit can further comprise an ear device described herein as a packaged set. Such packaged sets can further comprise instructions for use of the ear device as well as the apparatus.

Also disclosed herein are methods of making a kit, comprising assembling an apparatus described herein and instructions for use, and packaging the combination together in appropriate packaging. In some cases, an ear device described herein can also be added to the packaging.

Example 1—Foam Earplug

A foam earplug containing a ferromagnetic element in the form of a disk or sphere, as depicted in FIG. 2, is inserted into an ear using an insertion device. Briefly, the actuation switch of the device it flipped to the on position, thereby activating the electromagnet attached to the distal end of the insertion device. The ear device is attached to the insertion device through magnetic attraction between the electromagnet of the insertion device and the ferromagnetic element of the earplug. The insertion apparatus is introduced into the ear canal at a predetermined depth corresponding to the depth of the subject's ear canal. A flange attached to the proximal end of the insertion device prevents further insertion of the device and apparatus into the ear canal beyond the desired depth. The actuator switch is switched to the off position, thereby turning off the electromagnet and removing the magnetic attraction between the electromagnet and ferromagnetic element of the earplug. The insertion apparatus is then removed from the ear, leaving the earplug inserted deep within the ear canal of the subject.

Example 2—Covert Communication Device

An ear device designed for transmission of a Bluetooth signal and containing a ferromagnetic element is inserted into an ear using an insertion device. Briefly, a wireless actuation switch is depressed, thereby activating the electromagnet attached to the distal end of the insertion device. The ear device is attached to the insertion device through magnetic attraction between the electromagnet of the insertion device and the ferromagnetic element of the ear device. The insertion apparatus is introduced into the ear canal at a predetermined depth corresponding to the depth of the subject's ear canal. A flange attached to the proximal end of the insertion device prevents further insertion of the device and apparatus into the ear canal beyond the desired depth. The wireless actuator switch depressed again, thereby reversing the polarity of the electromagnet and creating a magnetic repulsion between the electromagnet and ferromagnetic element of the ear device. The insertion apparatus is then removed from the ear, leaving the ear device concealed deep within the ear canal of the subject. The ear device is then paired with a receiver device capable of receiving the Bluetooth signal.

Example 3—Retrieval of a Hearing Aid

A hearing aid containing a magnetic element that has previously been inserted into the ear of a subject can be retrieved using a retrieval device comprising a magnet that can be mechanically translated from a proximal end to a distal end of the apparatus through mechanical actuation of a pulley. The retrieval device is inserted into the ear of the subject while the magnet is in the proximal position. A flange attached to the proximal end of the insertion device prevents further insertion of the device and apparatus into the ear canal beyond the desired depth. The pulley is actuated to cause a translation of the magnet from the proximal end of the apparatus to the distal end, thereby producing a magnetic attraction between the hearing aid and the retrieval device. The retrieval device is then removed from the ear, thereby also removing the hearing device from the ear.

Example 4—Manipulation of Ear Plug with Magnetic Switch

Figure 12:
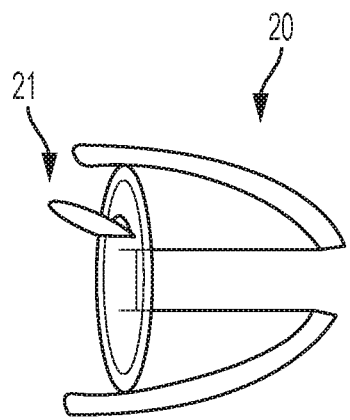
FIG. 12 depicts an earplug that comprises a magnetic switch that is maneuverable by a magnetic force to switch the earplug between "ON" and "OFF" states.
Figure 12:
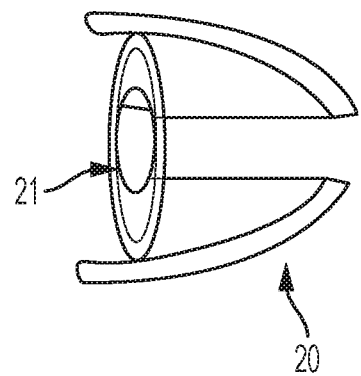

An ear device containing a magnetic switch can be manipulated by an apparatus disclosed herein. The magnetic switch is maneuverable by a magnetic force to switch the ear device between different work modes. FIG. 12 shows an ear device 20 that comprises a magnetic switch 21. In this case, the ear device 20 is an earplug that regulates pressure or acoustic waves transmitted therethrough to the ear at different efficiencies via the magnetic switch 21. As depicted in the figure, the magnetic switch 21 can be either in an "OFF" position, as shown in the upper panel, that leaves the earplug open to the pressure or acoustic waves to pass through, or in an "ON" position in the bottom panel, that blocks the earplug, so that the pressure or acoustic waves passing through can be blocked or attenuated. An apparatus as disclosed herein used to move the magnetic switch between "ON" and "OFF" positions can therefore switch the work modes of the earplug, in which the pressure or acoustic waves transmitted through the ear plug are regulated at different efficiencies.

Example 4—Stabilization of Magnetic Ear Phones

Figure 13:
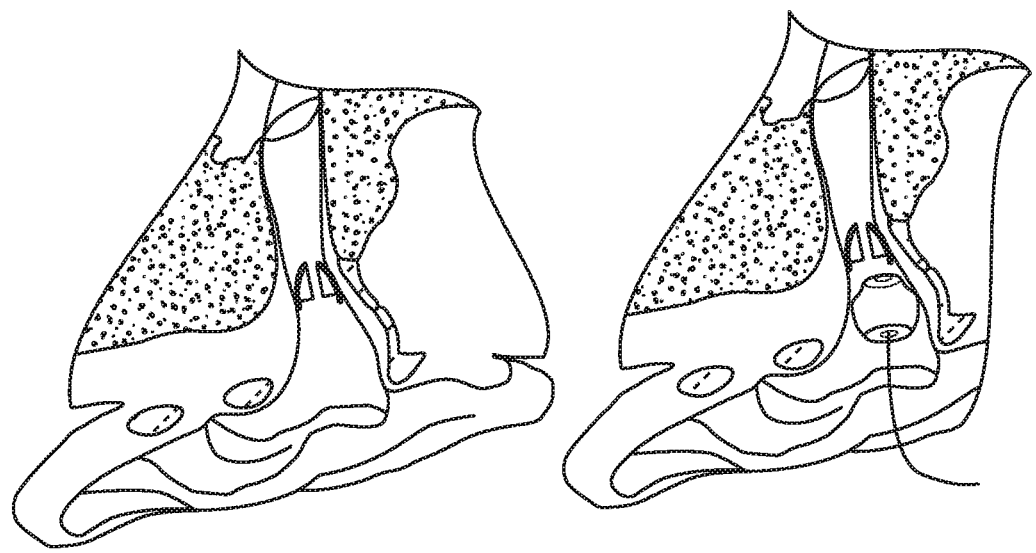
FIG. 13 depicts a magnetic earphone and a discoidal magnet, which work to ameliorate the loss of the ear phone from the ear.
Figure 13:
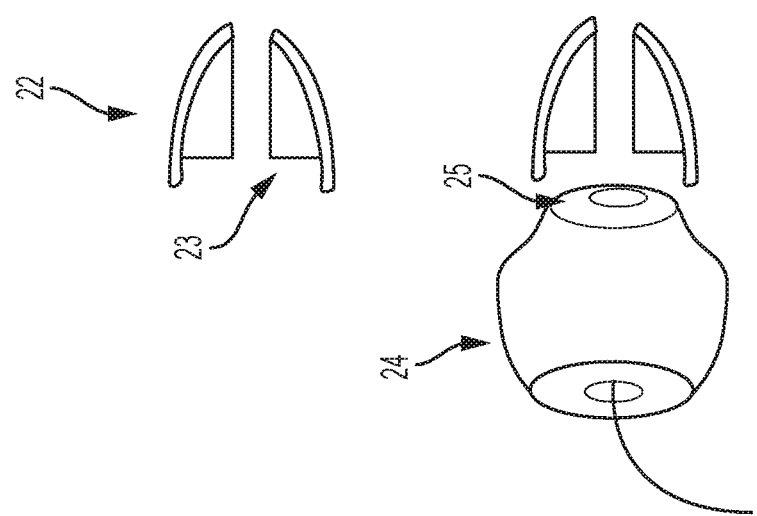

A discoidal magnet is inserted into an ear using an insertion device. Briefly, the actuation switch of the device is flipped to the on position, thereby activating the electromagnet attached to the distal end of the insertion device. The magnet is attached to the insertion device through magnetic attraction between the electromagnet of the insertion device and discoidal magnet. The insertion apparatus is introduced into the ear canal at a predetermined depth corresponding to the depth of the subject's ear canal. A flange attached to the proximal end of the insertion device prevents further insertion of the device and apparatus into the ear canal beyond the desired depth. The actuator switch is switched to the off position, thereby removing the electromagnetic attraction between the electromagnet and ferromagnetic element of the ear device. The insertion apparatus is then removed from the ear, leaving magnet within the ear canal of the subject. Magnetic ear phones are then inserted into the outer ear of the subject in such a manner to produce a magnetic attraction between the head phone placed on the outer ear and the magnet placed in the ear canal, thereby ameliorating loss of the magnetic ear phones relative to a subject lacking the magnet placed in the ear canal. FIG. 13 shows an exemplary set of the discoidal magnet and the magnetic ear phone. As shown in the figure, the discoidal magnet 22 comprises a magnetic element 23. It is first inserted into the ear canal using an insertion device (not shown) as shown in the upper right schematic. After removal of the insertion device (not shown), the magnetic ear phone 24 that comprises a magnet 25 is inserted into the outer ear to produce a magnetic attraction between the head phone and the discoidal magnet 22, as shown in the bottom right schematic.

Example 5—Alternative Designs

Figure 14:
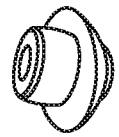
FIG. 14 shows a picture of an insertion tool and a removal tool, as well as a picture of earplugs with and without flange.
Figure 14:
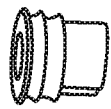
Figure 14:
Figure 14:

Referring to FIG. 14, pictures of an insertion tool, a removal tool picture, and earplugs with and without flange are shown. In the picture on the left, an insertion tool with offset from the end that has the magnet and a removal tool with flush at the magnet end are both shown. The offset from the magnet end constitutes the orientation restriction section according to some embodiments disclosed herein. The magnets of both the insertion tool and the removal tool as shown in the picture are static magnets.

Example 6—Alternative Grips

Figure 15:
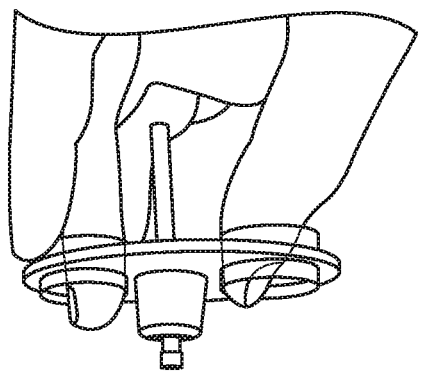
FIG. 15 shows pictures of two different types of gripping (handpiece grip and "Q-tip" grip) the apparatus disclosed herein.
Figure 15:
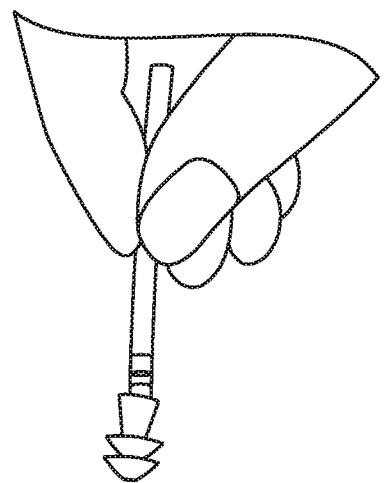
Figure 15:
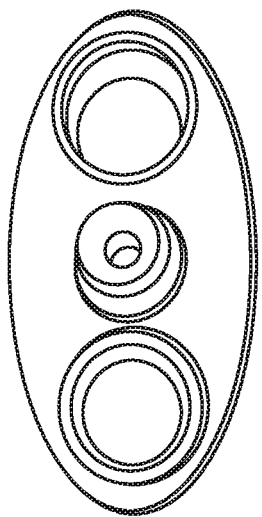
Figure 15:
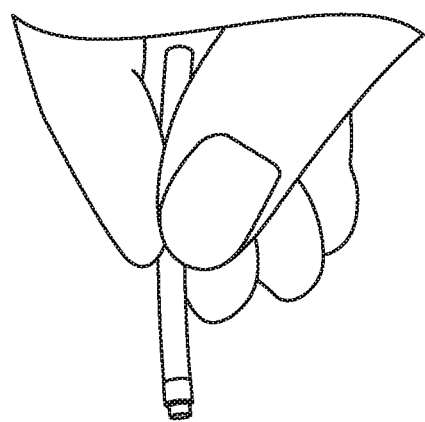

FIG. 15 shows pictures of two different manners of gripping the apparatus disclosed herein. The upper two pictures show a handpiece grip tool, which has two holes that fit for inserting two fingers of the operator's one hand and another hole for inserting the apparatus. The apparatus is thereby manipulated by the two fingers of the operator as shown in the upper right picture. The pictures at the bottom show the "Q-tip" type of grip, where the apparatus is gripped directly by two fingers of the operator's one hand, like a "Q-tip".

Example 7—Insertion of Ear Plug Using Fixed Magnet Apparatus

Figure 16:
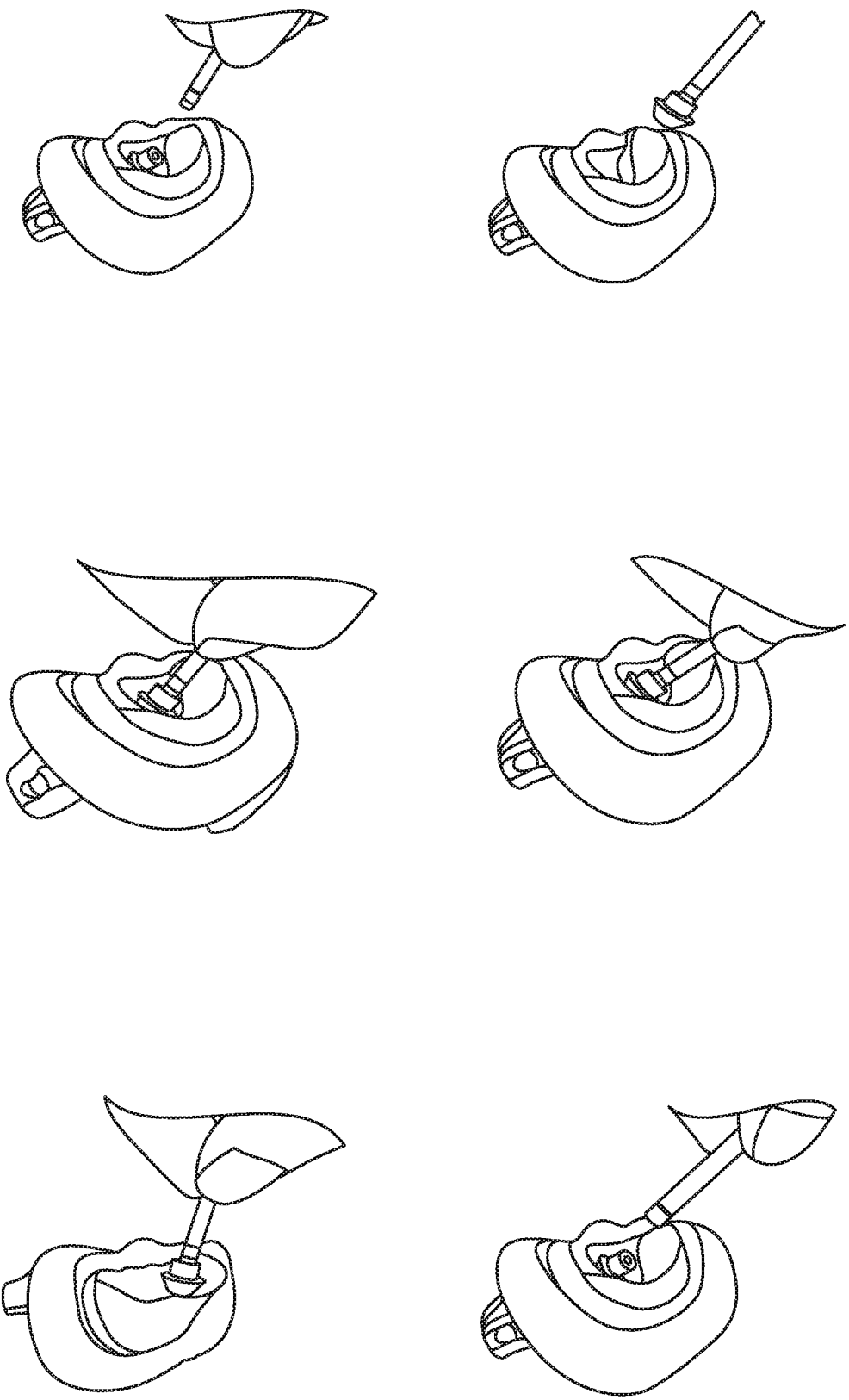
FIG. 16 shows a series of pictures demonstrating a process of inserting an earplug into an ear model and removing the earplug from the ear model using an insertion tool and a removal tool, respectively.

FIG. 16 shows a series of pictures demonstrating a process of inserting an earplug into an ear model and removing the earplug from the ear model using an insertion tool and a removal tool, respectively. The insertion tool, removal tool, and the earplug with flange in this figure are the same as shown in FIG. 14.

Briefly, an ear plug comprising a magnetic element is attached to an insertion comprising a fixed magnet through magnetic attraction. The ear plug is inserted into the ear canal at a predefined depth of about 2 cm. The insertion apparatus is removed from the ear, while frictional force retains the ear plug within the ear. The frictional force is sufficient to overcome the magnetic attraction from the insertion device, thereby resulting in retention of the ear device within the ear canal.

The ear device can be removed using a separate removal device. The removal device comprises a stronger magnet than the insertion device. Specifically, the removal device comprises a magnetic with sufficient strength to overcome the frictional force holding the ear device within the ear. Briefly, the removal device is inserted into the ear, causing magnetic attraction with the magnetic element of the ear plug. The removal device is removed from the ear, thereby removing the ear plug from the ear canal.

Example 8—Insertion of Ear Oximeter

An ear oximeter designed for measuring pulse, dissolved oxygen level, and blood pressure containing an iron ferromagnetic element is inserted into an ear using an insertion device that comprises an electromagnetic coil on a proximal end of the insertion device. Briefly, an actuation switch on the power source operatively linked to the electromagnetic coil is depressed, thereby activating the electromagnet. The ear oximeter is attached to the insertion device through magnetic attraction between the electromagnet of the insertion device and the ferromagnetic element of the ear device. The insertion apparatus is introduced into the ear canal at a predetermined depth of about 3 cm. A marker on insertion device is present and can be used to determine the appropriate depth. In this example, the marker lines up with the outside of the ear canal when the insertion device is inserted to the appropriate depth. The actuation switch depressed again, thereby powering off the electromagnet. The insertion apparatus is then removed from the ear, leaving the ear device concealed deep within the ear canal of the subject. The ear device is then paired with a receiver device capable of receiving the Bluetooth signal.

Example 9—Manipulation of Ear Plug

An ear plug 20 as substantially depicted in FIG. 12 is inserted as described above in Example 1. The ear plug 20 contains a flap 21 the comprises a magnetic element. A manipulation device configured with a weak fixed magnet similar to the insertion device of Example 7 can be used to manipulate the flap 21. The manipulation device can comprise the fixed magnet in an orientation such that the flap 21 is pulled either upwards or downwards by a rotation of the manipulation device. The fixed magnet of the manipulation device is strong enough to manipulate the flap 21, but is not strong enough to remove the ear plug 20 from the ear canal. A separate removal device as described in Example 7 can be used to remove the ear plug 20.

Example 10—Alternative Arrangement of Magnetic Element

Figure 11A:
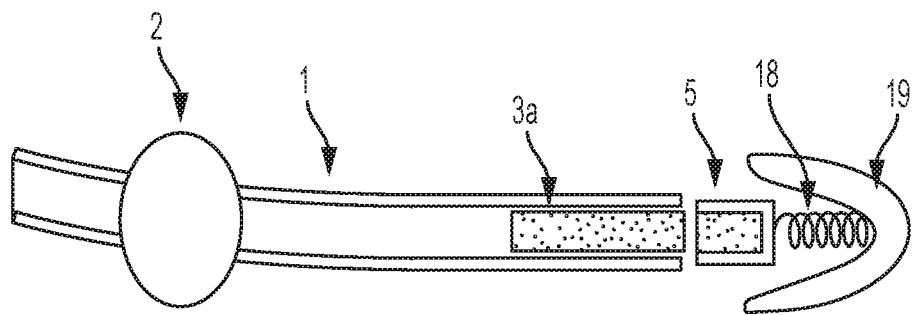
FIGS. 11A-11C depict a process of manipulating an ear device that comprises a spring that associates a magnet to the ear device.
Figure 11B:
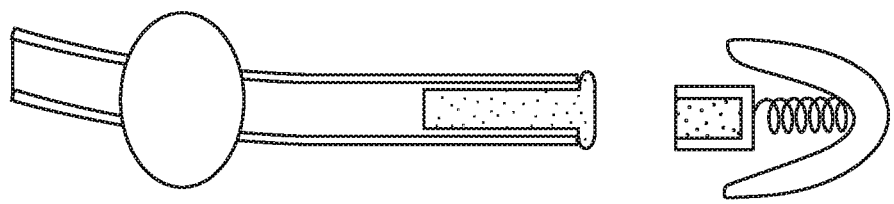
Figure 11C:
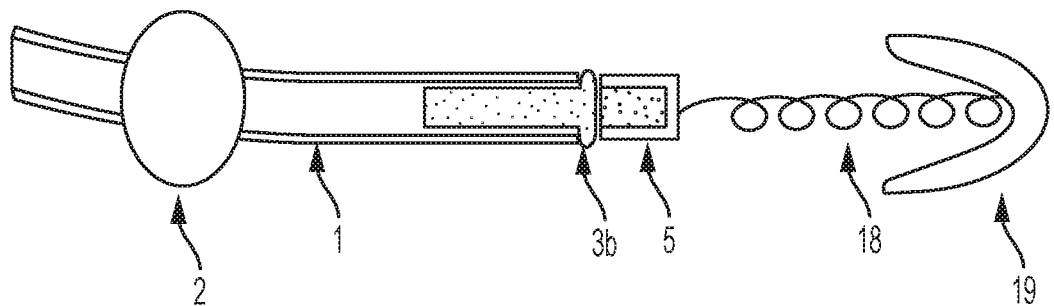

An ear device 19 as depicted in FIGS. 11A-11C can be inserted using an insertion device 1 comprising a fixed magnet 3a on a distal end of the insertion device 1. As shown in FIG. 11A, the insertion device contains a stop element 2 to prevent further insertion of the insertion device 1 into the ear canal. The ear device 19 comprises a ferrite magnetic element 5 attached to the ear device 19 by a spring 18. When fully inserted into the ear canal, the ear device 19 comprising the ferrite magnetic element 5 and spring 18 are not visible from the outside, and the spring 18 is in a relaxed position within the ear canal.

A removal device as depicted in FIG. 11B comprising a fixed magnet 3b on a distal end of the removal device can be used to remove the ear device 19. When the removal device is inserted into the ear canal, the ferrite magnetic element 5 is magnetically attracted to the magnet 3b. Removing the removal device from the ear allows the magnetic element 5 to be removed from the ear canal while retaining the ear device 19 within the ear canal. As shown in FIG. 11C, the spring 18 is in a stretched position in this configuration. The ear device 19 can be fully removed from the ear canal by pulling on the spring 18 and ferrite magnetic element 5 further using forceps or fingers.

While preferred embodiments have been shown and described herein, it will be obvious to those skilled in the art that such embodiments are provided by way of example only. Numerous variations, changes, and substitutions will occur to those skilled in the art without departing from the disclosure provided herein. It should be understood that various alternatives to the embodiments described herein may be employed. It is intended that the following claims define the scope of embodiments and that methods and structures within the scope of these claims and their equivalents be covered thereby.

What is claimed is:

1. An apparatus, for insertion of an ear device into, or removal of the ear device from, an ear of a subject, the apparatus comprising:
    (i) an elongated section;
    (ii) a stop section associated with the elongated section; wherein the stop section is configured to contact a portion of the ear of the subject when the elongated section is inserted into the ear of the subject, thereby preventing further insertion of the elongated section into the ear of the subject;
    (iii) an electromagnet associated with a first end of the elongated section; and
    (iv) a power source and a switch electronically connected to the electromagnet, wherein the switch is configured to electrically reverse a polarity of the electromagnet to provide a magnetic attraction or a magnetic repulsion between the electromagnet and a magnetic element of the ear device.

2. The apparatus of claim 1, wherein the elongated section is an arm.

3. The apparatus of claim 1, wherein the stop section is a flange.

4. The apparatus of claim 3, wherein the flange comprises a handle.

5. A method of removing an ear device comprising a magnetic element from an ear of a subject comprising:
    (i) inserting the apparatus of claim 1 into the ear of the subject;
    (ii) activating the electromagnet; thereby providing the magnetic attraction between the electromagnet and the magnetic element of the ear device; and
    (iii) removing the apparatus from the ear of the subject.

6. The method of claim 5, further comprising activating the switch on the apparatus prior to (ii).

7. The method of claim 5, wherein the magnetic element is associated with the ear device through a linker, and the removing comprises:
    (i) removing the apparatus from the ear of the subject until the magnetic element and at least a portion of the linker are outside of the ear; and
    (ii) removing the ear device from the ear of the subject.

8. The method of claim 7, wherein the removing the ear device comprises pulling the magnetic element, the linker, or both until the ear device is removed out of the ear.

9. A method of ameliorating loss of a magnetic wireless earphone comprising:
    (i) inserting the apparatus of claim 1 into an ear of a subject, wherein the apparatus is in contact with the ear device through the magnetic attraction between the electromagnet and the magnetic element of the ear device;
    (ii) deactivating the electromagnet; thereby removing the magnetic attraction between the electromagnet and the magnetic element of the ear device;
    (iii) removing the apparatus from the ear of the subject; and
    (iv) inserting the magnetic wireless earphone into the ear of the subject;
wherein the magnetic wireless earphone is magnetically attracted to the ear device.

10. The apparatus of claim 1, wherein the elongated section is flexible.

11. The apparatus of claim 1, wherein the elongated section is rigid.

12. A kit comprising:
    (a) the apparatus of claim 1;
    (b) instructions for use of the apparatus; and
    (c) the ear device.

13. The kit of claim 12, wherein the ear device is a communication device.

14. The kit of claim 12, wherein the ear device is an earplug, wherein the earplug comprises a foam material, and wherein the earplug is configured to at least partially regulate pressure or sound waves transmitted into the ear of the subject.

15. The kit of claim 12, wherein the ear device further comprises a noise canceling element, wherein the noise canceling element is configured to transmit destructive interference when engaged.

16. The kit of claim 12, wherein the ear device further comprises a magnetic field generator.

17. The kit of claim 12, wherein the ear device is a diagnostic device.

18. The kit of claim 12, wherein the ear device comprises jewelry, wherein the jewelry is non-piercing.

\* \* \* \* \*